United States Patent
Downs et al.

(10) Patent No.: US 6,723,555 B2
(45) Date of Patent: Apr. 20, 2004

(54) MULTI-SAMPLE FERMENTOR AND METHOD OF USING SAME

(75) Inventors: Robert Charles Downs, La Jolla, CA (US); Scott Allan Lesley, San Diego, CA (US); James Kevin Mainquist, San Diego, CA (US); Daniel Terence McMullan, San Diego, CA (US); Andrew J. Meyer, San Diego, CA (US); Marc Nasoff, San Diego, CA (US)

(73) Assignee: IRM, LLC, Hamilton (BM)

( * ) Notice: Subject to any disclaimer, the term of this patent is extended or adjusted under 35 U.S.C. 154(b) by 0 days.

(21) Appl. No.: 10/071,842

(22) Filed: Feb. 8, 2002

(65) Prior Publication Data

US 2002/0146818 A1 Oct. 10, 2002

Related U.S. Application Data

(63) Continuation-in-part of application No. 09/780,591, filed on Feb. 8, 2001, now Pat. No. 6,635,441.

(51) Int. Cl.$^7$ ............................................... C12M 1/00
(52) U.S. Cl. ........................... 435/289.1; 435/296.1; 435/813; 435/818; 99/276; 99/323.1
(58) Field of Search ..................... 435/286.6, 289.1, 435/296.1, 303.1, 304.1, 813, 818; 99/276, 323.1, 323.2

(56) References Cited

U.S. PATENT DOCUMENTS

| | | |
|---|---|---|
| 3,843,809 A | 10/1974 | Luck |
| 3,997,396 A | 12/1976 | Delente |
| 4,033,825 A | 7/1977 | Haddad et al. |
| 4,201,845 A | 5/1980 | Feder et al. |
| 4,680,266 A | 7/1987 | Tschopp et al. |
| 4,696,902 A | 9/1987 | Bisconte |
| 4,774,187 A | 9/1988 | Lehmann |
| 4,891,310 A | 1/1990 | Shimizu et al. |
| 4,904,601 A | 2/1990 | Mano et al. |
| 4,923,817 A | 5/1990 | Mundt |
| 5,057,428 A | 10/1991 | Mizutani et al. |
| 5,416,022 A | 5/1995 | Amiot |
| 5,443,985 A | 8/1995 | Lu et al. |
| 5,571,720 A | 11/1996 | Grandics et al. |
| 5,622,819 A | 4/1997 | Herman |
| 5,686,304 A | 11/1997 | Codner |
| 5,702,672 A * | 12/1997 | DeWitt et al. ............... 422/131 |
| 5,821,116 A | 10/1998 | Herman |
| 5,864,395 A | 1/1999 | Laurberg |
| 5,989,913 A | 11/1999 | Anderson et al. |
| 6,008,010 A | 12/1999 | Greenberger et al. |
| 6,063,618 A * | 5/2000 | Weuster-Botz et al. .. 435/294.1 |
| 6,083,763 A * | 7/2000 | Balch ......................... 436/518 |
| 6,093,551 A * | 7/2000 | Raithel et al. ............. 435/7.21 |
| 6,146,534 A * | 11/2000 | Grendze et al. ........... 210/635 |

OTHER PUBLICATIONS

Sigma Cell Culture Catalog, 1994., Sigma Chemical Company, St. Louis, p. 142.

* cited by examiner

*Primary Examiner*—David A. Redding
(74) *Attorney, Agent, or Firm*—Timothy L. Smith; Christopher C. Sappenfield; Quine Intellectual Property Law Group, P.C.

(57) ABSTRACT

A fermentation apparatus is constructed to produce a known and repeatable amount of untainted fermentation product using multiple fermentation vessels. To facilitate further processing compatible with other product processing steps, the fermentation apparatus has an array of sample vessels arranged in a container frame. The container frame is configured to hold the sample vessels during fermentation and to transport the vessel array to or from another processing station. Corresponding to the number of sample vessels in the sample vessel array, a cannula array is configured such that each cannula may be placed inside a sample vessel. The cannula array is attached to a gas distributor that delivers oxygen and/or one or more other gases from a gas source through the cannula into the sample vessel. Because the fermentation volume for each individual sample vessel is smaller than a bulk fermentation apparatus, the fermentation product yields are predictable and cell growth rates can be effectively optimized.

12 Claims, 17 Drawing Sheets

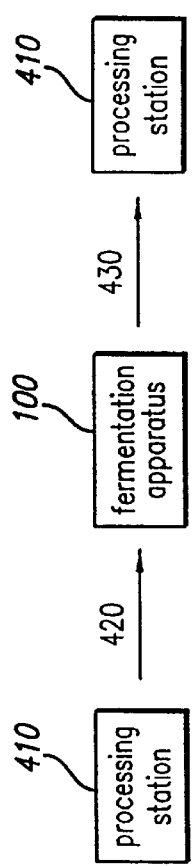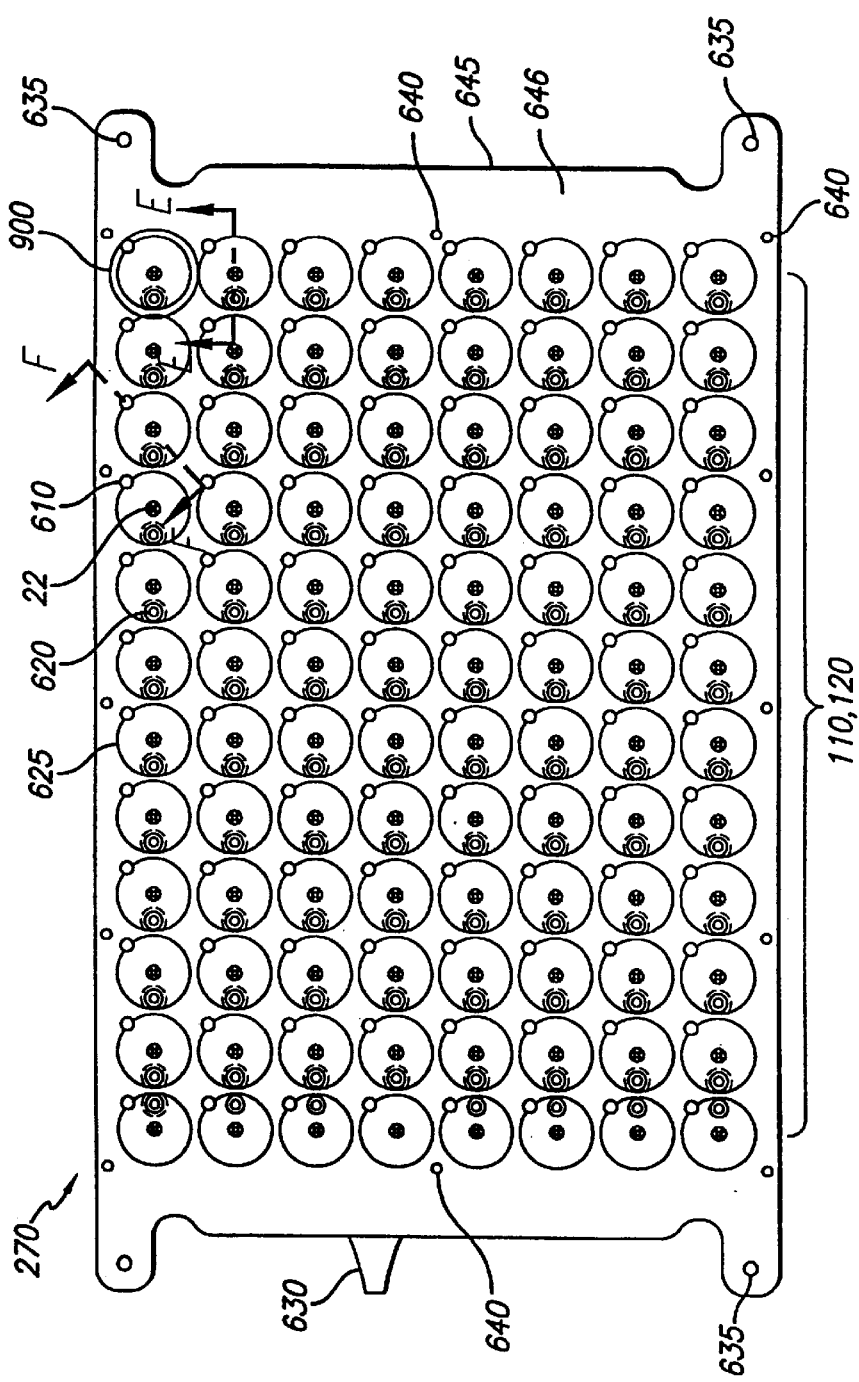
Fig. 5
Fig. 6

MULTI-SAMPLE FERMENTOR AND METHOD OF USING SAME

CROSS REFERENCE TO RELATED APPLICATIONS

Pursuant to 35 U.S.C. §120, and any other applicable statute or rule, the present application is a continuation-in-part of and claims benefit of and priority to U.S. patent application Ser. No. 09/780,591, filed Feb. 8, 2001 entitled "Multi-Sample Fermentor and Method of Using Same, now U.S. Pat No. 6,635,441," the disclosure of which is incorporated herein by reference in its entirety for all purposes.

COPYRIGHT NOTIFICATION

Pursuant to 37 C.F.R. 1.71(e), a portion of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Fermentation is a key technology in many fields and industries and is performed both on a mass production scale and on an experimental, bench top scale. For example, fermentation systems are used for the production of a large number of products such as antibiotics, vaccines, synthetic biopolymers, synthetic amino acids, and proteins. Fermentation technology is integral in the production of recombinant proteins using biological organisms, such as *E. coli*, and many other cell cultures. For example, production of commercial pharmaceuticals such as recombinant insulin (Eli Lilly), erythropoietin (Amgen), and interferon (Roche) all involve fermentation as an essential step.

In addition, the recent identification of the tens of thousands of genes comprising the human genome highlight an important use of fermentation, namely the production of the proteins encoded by those genes. The determination of each gene's function is of paramount importance and therefore, the proteins encoded by those genes must be produced, e.g., by fermentation methods. Because each gene encodes at least one protein, tens of thousands of proteins must be produced and isolated. However, fermentation and isolation of the resulting protein products typically requires several labor intensive and time-consuming procedures. Fermentation systems that can produce tens of thousands of different proteins, e.g., in amounts sufficient for analysis are therefore needed. An additional advantage would be fermentation systems that are amenable to high throughput processes and the microtiter plate format used in many biotechnolgy applications.

Although, rapid advances in biotechnology have enabled the development of high throughput alternatives to traditional laboratory bench top processes, fermentation methods have not been amenable to automation. For example, limits in current fermentation technology prevent the uninterrupted processing flow that characterizes automated high throughput systems. Existing fermentation systems typically involve multiple handling steps by either a batch processing method or a continuous processing method.

Fermentations are typically carried out in batch mode or continuous mode. Batch mode processes are those in which a fermentor is filled with a medium in which cells are grown and the fermentation is allowed to proceed with the entire contents removed from the fermentor at the end for downstream or post-processing. The fermentor is then cleaned, re-filled, and inoculated for the fermentation process to be performed again. For example, current production scale batch processes involve first fermenting in large scale, bulk fermentation vessels, then processing the fermentation medium to isolate the desired fermentation product, followed by transferring this product into the production stream for further processing, and finally cleaning the fermentation apparatus for the next batch. In a large scale batch culture, it is generally necessary to provide a high initial concentration of nutrients in order to sustain cell growth over an extended time. As a result, substrate inhibition may occur in the early stages of cell growth and then may be followed by a nutrient deficiency in the late stages of fermentation. These disadvantages result in sub-optimal cell growth rates and fermentation yields. Another disadvantage of this method lies in the need to individually dispense the fermentation products from the bulk fermentation apparatus into separate sample vessels for further processing. Thus, by producing the fermentation product on a bulk scale, the fermentation product is not immediately available for automated processing. Further disadvantages include the decreased efficiency of both transferring the material to another sample vessel, as well as cleaning and sterilizing the fermentation apparatus for the next batch. These disadvantages result in increased production costs, inefficient production times and decreased yields.

Continuous batch processes involve siphoning off the fermentation product from the bulk fermentation vessel and continuously adding nutrients to the fermentation medium according to a calculated exponential growth curve. This curve, however, is merely an approximation that does not accurately predict cell growth in large, industrial scale quantities of fermentation medium. Consequently, due to the unpredictable nature of large scale fermentation environments, experienced personnel are required to monitor the feeding rate very closely. Changes in the fermentation environment may result in either poisoned fermentation products being siphoned off into the production stream or sub-optimal production yields due to starved fermentation mediums. As a further disadvantage, unpredictable fermentation product yields affect the accuracy of subsequent processing steps. For example, when the fermentation yield decreases, the amount of aspirating, the amount of reagent dispensed, or the centrifuge time is no longer optimized, or even predictable. Frequent or continuous monitoring of the fermentation process and adjustment of the fermentation conditions is often not practicable or efficient in a production scale process.

Neither of the current processes provides an efficient, automated production scale fermentation. However, fermentation remains a key processing step in a number of industries, particularly in biotechnology industries, and thus a need exists for incorporating fermentation processes into automated high throughput systems. A process that produces a precise, known, and repeatable amount of untainted fermentation product with limited human interaction or sample vessel transfer is essential to integrating fermentation into modern production processes. The present invention meets these as well as other needs that will be apparent upon review of the following detailed description and figures.

SUMMARY OF THE INVENTION

The present invention provides methods and apparatuses for simultaneously fermenting a plurality of samples, e.g., small samples in an 8 by 12 array. For example, the present invention provides a fermentation apparatus comprising a container frame configured to contain a plurality of sample vessels and a gas distribution arrangement coupled to the container frame. The fermentor provides for fermentation of large numbers of samples, e.g., to produce a large number of proteins. Alternatively, the fermentors of the invention provide a more efficient route for production scale fermentations.

In one aspect the invention provides a container frame configured to contain a plurality of sample vessels, e.g., in an array; and, a gas distribution arrangement configured to provide gas to a plurality of sample vessels, e.g., when the sample vessels are positioned in the container frame. The container frame is typically configured to contain an array of sample vessels, e.g., an 8 by 12 array, e.g., holding at least about 96, 384, or 1536 samples. The gas distribution arrangement typically comprises a gas inlet configured to deliver gas to a plurality of cannulas, which are configured to provide gas to the sample vessels.

In one embodiment, the container frame is a transportable container frame, e.g., configured for transport to a post-fermentation processing station. In addition, the container frame is optionally configured for placement within a temperature controlled area, e.g., water bath or a temperature controlled room, wherein a temperature controller is coupled to the container frame and/or to one or more sample vessels within the container frame.

In other embodiments, the container frame is autoclavable. For example, the container frame is autoclavable on its own or in combination with the gas distribution arrangement and/or the sample vessels.

The sample vessels typically comprise glass, plastic, metal, polycarbonate, ceramic, or the like. Each sample vessel typically has a volume of about 50 to 100 ml, e.g., and is used to hold a sample comprising less than about 80 mls, more typically about 65 mls. The samples in the plurality of sample vessels each have substantially the same composition or different compositions, e.g., to produce a large quantity of a single protein, or to produce multiple proteins simultaneously.

In other embodiments, the sample vessels optionally comprise a vent, e.g., for releasing built up pressure during fermentation. Sensors are also optionally placed in contact with one or more of the samples in the sample vessels, e.g., for monitoring temperature, pH, and the like.

In one embodiment, the gas distribution arrangement comprises a dispensing plate, an array of sample vessel areas, an array of cannulas, and a gas inlet. The dispensing plate typically comprises a top portion and a bottom portion that are joined together such that a hollow space exists between them. The array of sample vessel areas is typically located in a bottom surface of the bottom portion. Each sample vessel area comprises a recess and is positioned to correspond to the array of sample vessels. The array of cannulas are typically in fluid communication with the hollow space and protrude from a bottom surface of the dispensing plate through the sample vessel areas, e.g., to provide gas flow to the sample vessels. In some embodiments, the cannulas comprises a plurality of passages, e.g., at least three passages. The gas inlet is typically in fluid communication with the hollow space for delivering gas into a plurality of sample vessels via the cannulas during fermentation. For example, the gas distribution arrangement in some embodiments comprises a gas source that provides oxygen or a mixture of oxygen and at least one other gas to each sample vessel during operation of the apparatus.

In other embodiments, the gas distribution arrangement is optionally configured to allow delivery of one or more reagents to the sample vessels. For example, a dispenser is optionally coupled to the gas distribution arrangement, e.g., for dispensing one or more reagents into the plurality of sample vessels. The dispenser is typically configured to dispense reagents into the plurality of sample vessels, e.g., via a plurality of apertures corresponding to the sample vessels.

In addition, a process controller is operably coupled to the gas distribution arrangement, e.g., for controlling and/or monitoring gas flow to the plurality of sample being fermented.

In another aspect, the present invention provides a fermentor head for multiple sample fermentation. A typical fermentor head comprises a dispensing plate that comprises a top portion and a bottom portion, an array of sample vessels areas, an array of cannulas and a gas inlet. The bottom portion and the top portion of the dispensing plate are joined together such that a hollow space exists between them. The array of sample vessel areas is typically located in a bottom surface of the bottom portion of the dispensing plate, which sample vessel areas each comprise a recess and are positioned to correspond to an array of sample vessels. The array of cannulas are typically in fluid communication with the hollow space and protrude from a bottom surface of the dispensing plate through the sample vessel areas, e.g., 15 to 16 cm; with the gas inlet in fluid communication with the hollow space for delivering gas into a plurality of sample vessels via the cannulas during fermentation. Typically, the cannulas deliver gas adjacent to a bottom of the sample vessels. In some embodiments, the dispensing plate further comprises an array of apertures for accessing samples during fermentation. Alternatively, the cannulas are adapted to deliver gas, deliver fluid, or aspirate fluid from the sample vessels during fermentation. The vessels and samples used with the fermentor head typically correspond to those described above.

In another aspect, the present invention provides a method of fermenting a plurality of samples. The method typically comprises providing a plurality of sample vessels in a container frame, wherein each of the sample vessels contains a sample. The samples in the plurality of sample vessels are typically fermented, which fermenting comprises simultaneously delivering gas, e.g., oxygen, air, and/or nitrogen, to each of the sample vessels via a plurality of cannulas associated with the sample vessels. Each sample typically has a volume of less than 100 ml, e.g., using sample vessels and a container frame as described above. In some embodiments, delivering gas to the samples comprises delivering air and oxygen to the samples over a period of time, during which period of time, the ratio of air to oxygen changes, e.g., linearly over time or in a stepwise manner over time.

In some embodiments, the methods further comprise detecting one or more fermentation conditions with a sensor coupled to one or more sample vessels and adjusting the fermentation conditions in the sample vessels, e.g., at predetermined time intervals. For example, adjusting the fermentation conditions optionally comprises adding a feed solution to the sample vessels. Detecting optionally comprises measuring a pH of one of the samples; measuring a redox potential of one of the samples; measuring an optical density of one of the samples; and/or measuring a light emission from one of the samples.

In some embodiments, the methods further comprise pre-processing or post-processing the samples in the same set of sample vessels, e.g., in the same or a different location as the fermentation step. In some embodiments, the pre-processing and/or post-processing are performed robotically. Pre-processing and/or post-processing steps include, but are not limited to, centrifugation, aspiration, and/or dispensing of one or more reagent. For example, the methods optionally comprise transferring the sample vessels into a centrifuge rotor after fermentation or autoclaving the sample vessels, e.g., in the container frame prior to fermentation. In addition, the cannulas are also optionally autoclavable with the container frame.

In another aspect, the methods of the invention comprise positioning a plurality of sample vessels into a transportable container frame, which container frame maintains the sample vessels in an array. The plurality of samples is optionally placed into the plurality of sample vessels, e.g., before or after the vessels are positioned in the frame. A fermentor head is typically attached to the container frame, e.g., prior to or after the samples have been added to the vessels. The fermentor head typically comprises an array of cannulas, e.g., as described above. The cannulas typically correspond to the array of sample vessels and are inserted into the sample vessels when the fermentor head is attached. The samples in the sample vessels are then fermented, e.g., by simultaneously delivering a gas, e.g., oxygen, nitrogen, and/or air, to the samples via the array of cannulas. In some embodiments, the fermentation is an anaerobic fermentation comprising delivering an inert gas to maintain anaerobic fermentation conditions in the sample vessels. The methods optionally comprise robotic steps pre-processing steps, and/or post processing steps as described above. For example, the sample vessels and/or the sample container used in the above methods are optionally configured to be compatible with a centrifuge, wherein the method further comprises transporting the container frame and/or sample vessels to the centrifuge for centrifugation.

In some embodiments, the methods comprise transportation to an aspirator or dispenser, wherein the aspirator typically comprises an aspirator head which corresponds to the array of sample vessels within the container frame, in which case, the method further including operably attaching the aspirator head to the sample vessels and simultaneously aspirating the samples within the sample vessels. In other embodiments, a dispensing step is included, wherein the dispenser comprises a dispensing head corresponding to the array of sample vessels and the method further includes operably attaching the dispenser head to the sample vessels and simultaneously dispensing one or more materials into the sample vessels.

In another embodiment, the present invention provides a method of processing a plurality of fermentation samples. The method comprises fermenting a plurality of fermentation samples in a plurality of sample vessels, resulting in a plurality of fermented samples; robotically transporting the sample vessels containing the fermented samples to a centrifuge head; and centrifuging the fermented samples in the same sample vessels in which the fermentation was performed. For example, about 4 to about 10 sample vessels are optionally robotically transported to the centrifuge head at the same time. The method also optionally includes isolating a supernatant from the sample vessels after centrifuging the fermentation samples.

BRIEF DESCRIPTION OF THE FIGURES

FIG. 5 is a block diagram showing the use of a fermentation system within a multiple process procedure in accordance with the present invention.

FIG. 6 is a schematic illustrating a bottom view of a gas arrangement in accordance with the present invention.

DETAILED DISCUSSION OF THE INVENTION

Figure 1:
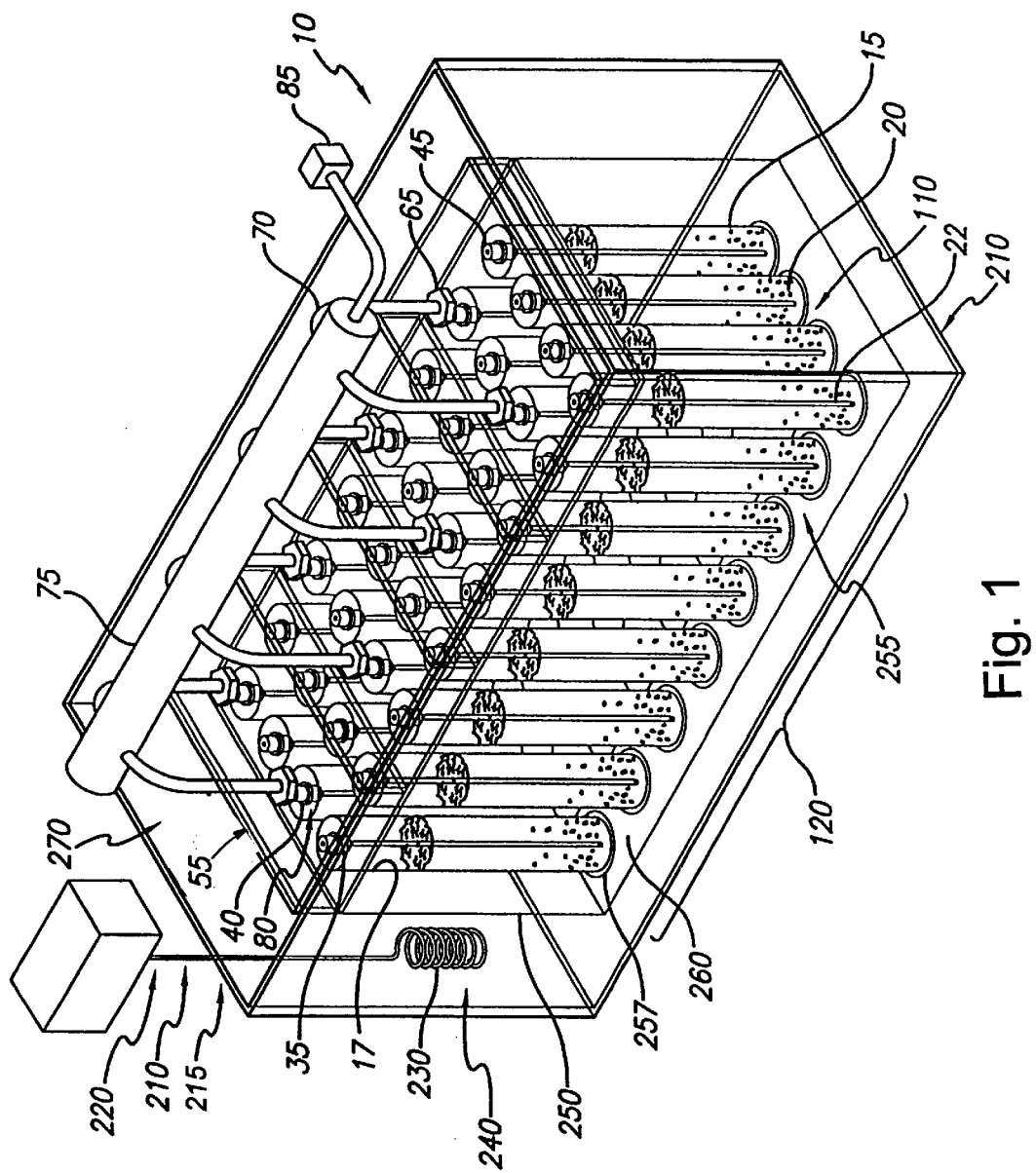
FIG. 1 is a schematic showing a perspective view of a fermentation apparatus in accordance with the present invention.

The present invention provides a fermentation apparatus and methods of fermentation. The fermentors and methods presented herein provide production scale fermentation, e.g., automated high throughput fermentation, as described below. For example, the present invention provides a multi-sample fermentor comprising a transportable container frame. The fermentor is configured to simultaneously ferment a plurality of samples held in an array of sample vessels within a container frame. The sample vessels provide relatively small volume batch fermentations, e.g., about 50 ml to 80 ml of sample in each sample vessel, more typically 65 ml. In addition, the transportable container frame provides a high throughput aspect to the system that has been absent in previous fermentation systems. The container frame is used to provide processing, e.g., upstream or downstream processing in the same sample vessels.

The present invention provides a novel fermentor apparatus that allows batch mode fermentation using a plurality of small samples. For example, small sample sizes overcome the disadvantage of sub-optimal growth rates and yields that exist in large batch mode processes. In addition, the present system eliminates the need for sample handling for post-fermentation processing. The sample vessels in the present invention are used directly in any post-processing steps, which eliminates many cleaning and sterilizing steps as well, thereby providing a less expensive, more efficient, and faster fermentation process.

The present invention also overcomes the disadvantages of the continuous feed systems, e.g., with the small sample sizes used. For example, the estimated growth curves used in large scale continuous feed processes are unnecessary in the present invention. Therefore, the unpredictable results and frequent monitoring of continuous feed processes are not a problem in the present invention.

The present invention provides a fermentation apparatus that solves the above problems, e.g., by using small sample sizes and fermenting the multiple samples simultaneously. By simultaneously performing multiple fermentations, e.g., small scale fermentations, in batch mode, optimal mixing is achieved, optimal temperature and pH can be maintained as well as many other advantages that will be apparent upon further reading of the present description.

I. A Multi-sample Fermentation Apparatus

The present invention provides a multi-sample fermentation apparatus. Typically, the apparatuses of the invention comprise a sample holder or container frame and a gas distribution system. For example, in one embodiment, a container frame is used to hold and/or transport an array of sample vessels for fermentation. A fermentor head, e.g., comprising an array of cannulas corresponding to the array of sample vessels, is coupled, e.g., directly, to the container frame and/or sample vessels. Gas is distributed into the multiple sample vessels via the cannulas and fermentor head providing multi-sample fermentation. Various components of the apparatuses are described in more detail below followed by methods of using the apparatuses and example fermentors.

A Container Frame is Used to Hold a Plurality of Sample Vessels

A "container frame" as used herein refers to an arrangement that holds and/or maintains a plurality of sample vessels in a desired arrangement. Typically, the container frames of the invention are transportable and autoclavable. In addition, they typically have no movable parts. A transportable container frame is one that is easily transported or moved while holding the sample vessels in the desired arrangement. For example, a container frame of the invention optionally has handles for transportation to a processing station, e.g., after fermentation is complete. An autoclavable container frame is one that can be placed directly in an autoclave for sterilization, e.g., including the sample vessels and samples if desired.

By using a transportable container frame, the entire array of sample vessels is optionally transported to and from one fermentation processing station to another processing station in a multiple process production. For example, a transportable container frame is optionally used to transport an array of sample vessels into a temperature controlled area such as a water bath, e.g., a water bath controlled by a temperature controller and temperature coil immersed in the water bath. Other forms of temperature control are also optionally used, such as temperature controlled gel baths, ovens, glove boxes, or air chambers.

Typically, the container frame maintains the sample vessels in an array, e.g., a rectangular array. In an embodiment shown in FIG. 1, individual sample vessels 15 are configured in a rectangular array, but the array is optionally configured in any physical construct that is conducive to fermentation or that is compatible with other processing steps. For example, a honeycomb, circular, triangular, or linear configuration may be more efficient in other contemplated applications of the present invention.

The container frames of the present invention typically have a plurality of placement wells for positioning the plurality of sample vessels, e.g., in an array. For example, the placement wells optionally comprise indentations in the bottom of a container frame, into which sample tubes are optionally placed. In addition to the indentations or wells in the bottom of the container frame, the container frames optionally include an upper portion, e.g., for supporting the tops of the sample tubes and maintaining their position. Example container frames are shown in FIG. 1 (container frame 250) and FIG. 13 (container frame 1300).

Figure 13:
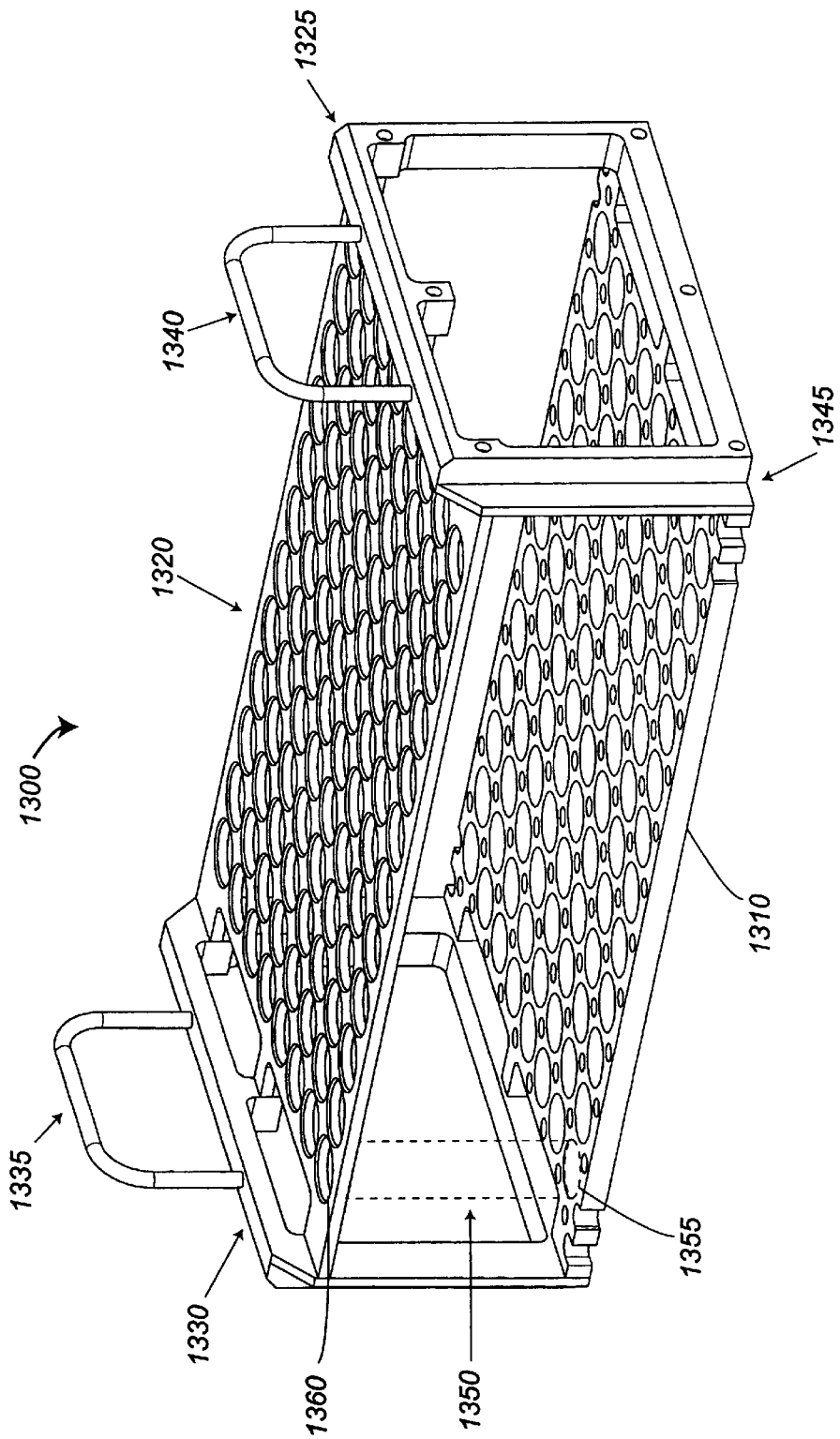
FIG. 13 is a schematic drawing that illustrates a container frame for maintaining a plurality of sample vessels in an array configuration.

For example, the bottom of each individual sample vessel is typically positioned within a placement well, e.g., placement well 257 in FIG. 1 or placement well 1350 in FIG. 13. The array of placement wells preferably mirrors the configuration of the sample vessel array and is embedded in the transportable container frame. Placement wells may, however, be arranged in alternative configurations. For example, placement wells may be arranged as linear troughs, each holding a row of sample vessels. In another embodiment, placement wells are absent from the transportable container frame. For example, the container frame optionally has a solid bottom surface with no indentations or wells. The sample vessels are then positioned in the frame, e.g., tightly packed against the sides of the frame to maintain the array configuration.

Sample vessels of the present invention typically comprise test tubes, other sample tubes, jars, flasks or any other container for holding a sample. Typically, the sample vessels have a volume of about 50 to about 200 milliliters, more typically about 80 to about 100 ml. The sample vessels are typically placed in an array of placement wells in a container frame, e.g., for autoclaving, processing, fermentation, and the like.

In some embodiments, the sample vessels are constructed of Pyrex glass or polycarbonate, but other suitable materials are optionally used to construct the sample vessels. For example, plastic, ceramic, metal, e.g., aluminum, or any other material is optionally used that is non-reactive to fermentation medium or to other materials involved in additional processes contemplated in a multiple process production, such as in a high throughput system. It will further be appreciated that the fermentation medium may be the same medium in each individual sample vessels or, alternatively, the array of sample vessels optionally includes a combination of different fermentation mediums. For example, fermentation medium may be the same in each individual sample vessel and contain the same fermentation broth for a bulk synthetic process. Alternatively, each sample vessel in an array may have a slightly different fermentation broth in order to optimize the production yield of a certain component.

In some embodiments, sample vessels with gripper surfaces are optionally used. In this embodiment, the container frame typically comprises a corresponding gripper surface, e.g., for maintaining the vessels in the desired configuration or to aid in transporting the array of sample vessels to and from a fermentation station and/or processing station.

In other embodiments, sensors are optionally included in the sample vessels of the invention. For example, a pH or temperature sensor is optionally positioned proximal to or within a sample vessel to monitor the fermentation reaction.

Fermentation samples are optionally placed in the sample vessels prior to their placement in the container frame or after such placement. In one embodiment, colonization of bacteria and other preparative steps are performed within the sample vessels, e.g., while they are contained in the container frame. For example, bacteria and initial nutrients are dispensed into each sample vessel at a prior processing station. Being able to prepare bacteria directly in each individual sample vessel eliminates the need to inoculate a culture and initiate colonization in a separate container before transferring the sample to the fermentation apparatus. Using the container frame arrangement of the present invention to colonize the fermenting bacteria decreases costs by eliminating a separate colonization arrangement. Once bacteria are colonized, sample vessels are conveniently transported, e.g., within the container frame, to a fermentation station, e.g., a water bath or any other temperature controlled area, such as a heated room. At the fermentation station or any time prior, a gas distribution arrangement is attached to the container frame to bubble gas into each sample vessel for fermentation. The gas distribution arrangements are described in more detail below.

A Gas Distribution Arrangement is Used to Provide Gas to a Plurality of Sample Vessels The gas distribution arrangement is used to provide gas flow to the sample vessels during fermentation. The gas distribution system typically comprises a gas inlet which is configured to flow gas from a gas source into a plurality of sample vessels in a container frame. Typically, the gas distribution arrangement is attached to the container frame, e.g., placed on top or screwed down. For example, the gas distribution arrangement typically comprises or is coupled to a plurality of cannulas through which the gas is flowed. The cannulas extend into each sample vessel for delivery of gas, e.g., to the bottom of the sample vessel. Such cannulas also optionally provide agitation of the sample within the sample vessel.

A gas source typically comprises a source of one or more gases, for example, air and oxygen. For example, in one embodiment the gas source contains an inlet for $N_2$ gas and an inlet for $O_2$ gas. The ratio of each gas can be controlled either manually or remotely by using a process controller. The ability to adjust gas ratios enables the present invention to optimize the amount of gas, e.g., oxygen, needed as the growing conditions change throughout the fermentation. For example, a process controller is optionally used to linearly change the ratio of air/oxygen over the course of a fermentation. Alternatively, the ratio is changed stepwise as fermentation proceeds. Any type, mixture, or number of gases are optionally introduced and mixed through the gas sources of the invention and provided to fermentation samples contained in one or more sample vessels, e.g., through a set of cannulas.

A cannula is a small tube for insertion into a duct or vessel, e.g., a fermentation sample vessel or tube as provided herein. In the present application, the cannulas are positionable inside the plurality of sample vessels, e.g., they typically comprise flexible or rigid tubes that are inserted into sample vessels for the delivery of various gases into the sample vessels. In one embodiment, the cannulas are arranged into an array, which array typically corresponds to an array of sample vessels. An example array of the invention comprises an 8 by 12 member array of sample vessels each having an associated rigid cannula. Typically, a cannula extends substantially to the bottom of each individual sample vessel in order to increase aeration and mixing. For example, the cannula optionally extend about 15 to about 16 cm from the bottom surface of a gas distribution arrangement. In some embodiments, two or more cannulas are provided in each sample vessel.

Figure 8:
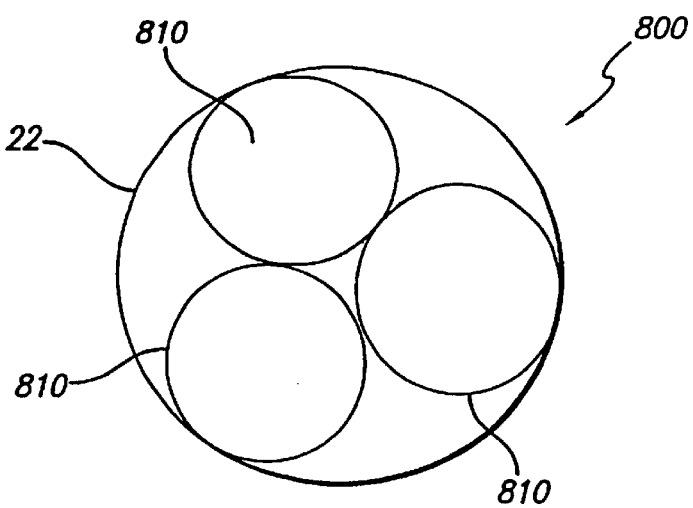
FIG. 8 is a cross sectional view of a cannula in accordance with the present invention.

In the embodiment illustrated in FIG. 8, gas flows through cannula 22 through three passages. Gas flow through passages are optionally individually or collectively regulated. Smaller gas bubbles are obtained with multiple small passages than with a single, larger passage through the cannula. As a result, gas bubbles formed from these multiple passages have more surface area than bubbles formed from a single passage. In a preferred embodiment, passages are precision drilled in order to more accurately adjust gas flow within each passage and to ensure uniform gas delivery across the set of sample vessels. Fewer or more passages may be used according to the specific application of the present invention. For example, the cannulas typically have about 1 to about 5 passages, more typically, 2 or 3 passages. Passages are optionally the same or different sizes and may be circular or any non-circular shape, such as rectangular, oval, or triangular.

In one embodiment cannula are included in a cannula assembly comprised of an array of individual cannulas corresponding to the plurality of sample vessels. Each individual cannula is optionally connected by a fastener which couples the cannula to a gas distribution arrangement.

Figure 12:
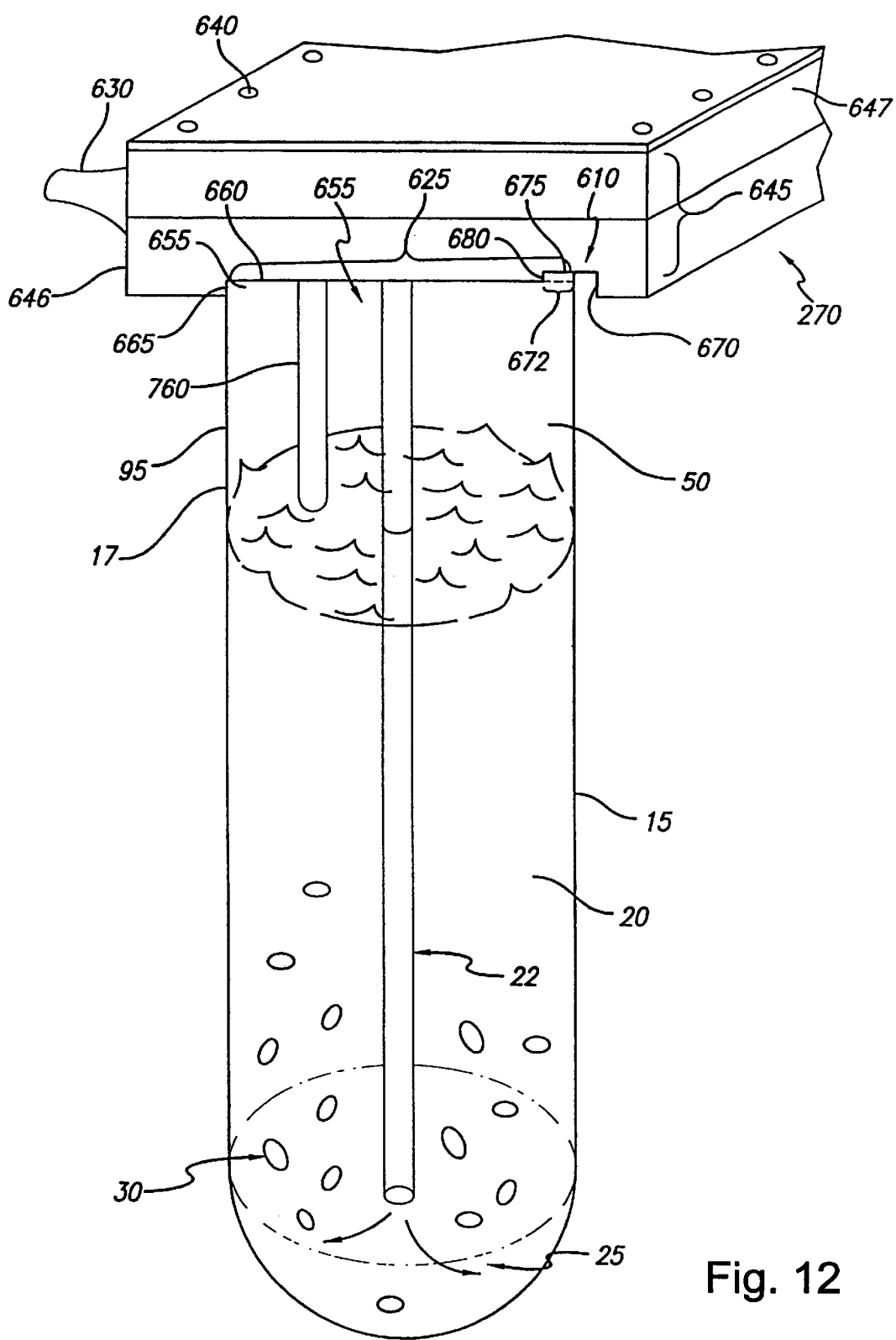
FIG. 12 is a schematic showing a perspective view of a fermentation sample vessel employing a dispensing plate in accordance with the present invention.
Figure 14:
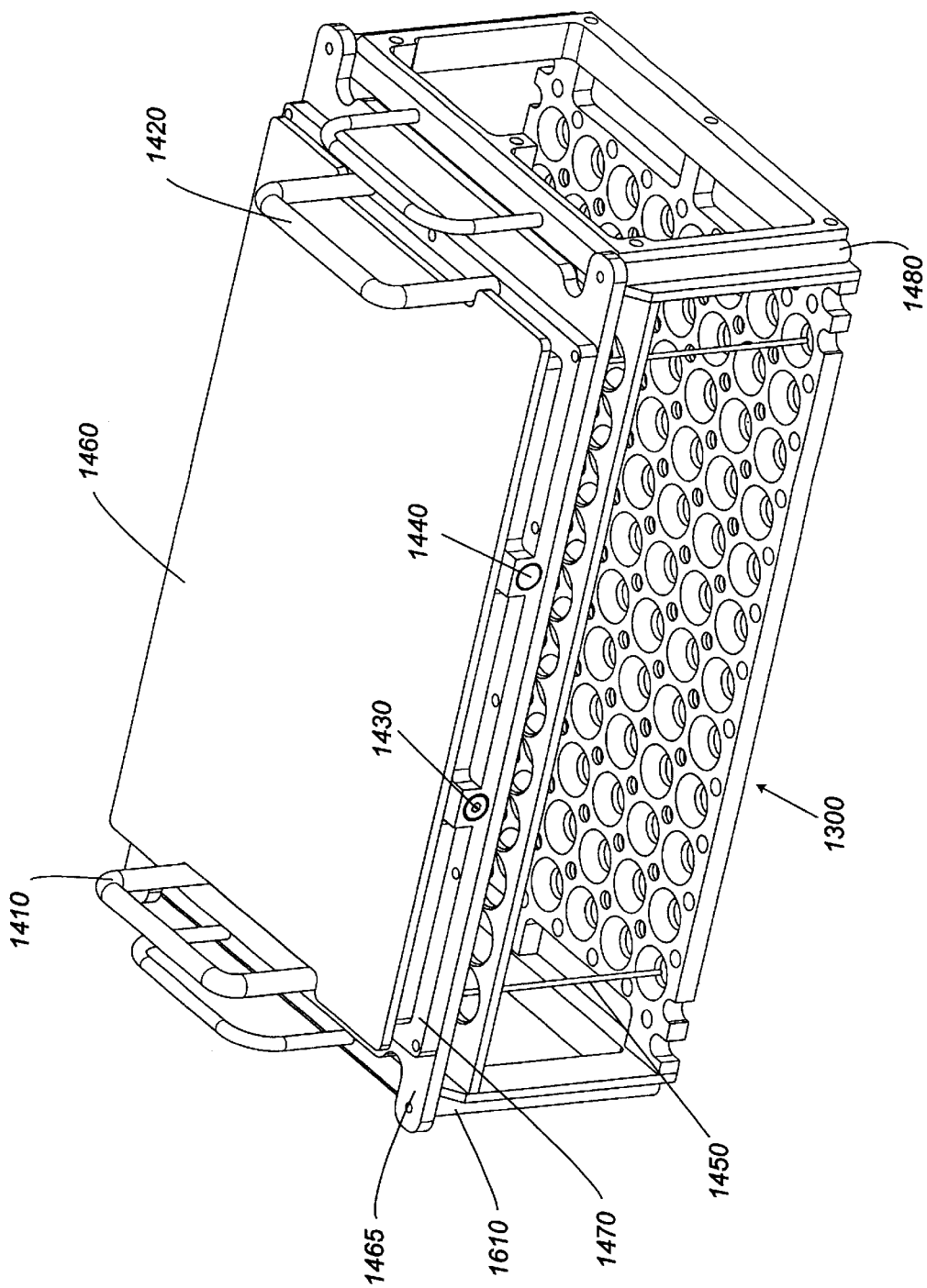
FIG. 14 is a schematic drawing that illustrates the container frame of FIG. 13 coupled to a gas distribution arrangement.

Gas, e.g., oxygen or an oxygen/air mixture, is delivered, e.g., from a manifold or other distribution system, to the sample vessels via the cannulas, thus oxygenating, if desired, the entire array of sample vessels within the container frame. For example, a gas source is optionally coupled directly to the gas distribution arrangement, e.g., with or without the use of a manifold, as illustrated in FIGS. 6, 12, and 14.

In this manner, the exact mixture of gases delivered from the gas source is uniformly distributed to each individual cannula assembly. Any gas distribution arrangement is optionally employed that uniformly delivers oxygen, an oxygen containing mixture, or another gas or gas mixture capable of fermenting the sample, from a gas source into the plurality of sample vessels. Example gas distribution arrangements are provided in FIGS. 1, 3, 12, and 14, which are described in more detail in the examples provided below.

In some embodiments, the gas distribution arrangement is comprised of one or more plates attached to an array of cannula, e.g., using a manifold, and a gas inlet, which delivers oxygen, an oxygen containing gas mixture, or another gas or gas mixture capable of fermenting the sample, to the sample vessels via the cannula.

Typically, the plates are aligned and fastened together, e.g., to form an air-tight, liquid-tight seal. A hollow space or interior space typically exists between the plates or within one of the plates through which gases are uniformly distributed to the associated cannula array. Any suitable fastener may be used. For example, guide pins, rivets, nails, nut/bolt combinations, or magnets may be used. A releasable fastener, such as a screw or nut/bolt combination, is used in a preferred embodiment, although permanent type fasteners, such as adhesives, may be desired in some applications. Vertical supports are optionally attached to the gas distribution arrangement, thus supporting the arrangement on an array of sample vessels.

The plates are optionally composed of any suitable material that maintains the structural integrity of the plate during fermentation. For example, a plate is optionally composed of metal, plastic, ceramic, or any suitable composite. In one example, the plates comprise Teflon™-coated aluminum, thus enabling the plates to undergo autoclave sterilization procedures along with the container frame and sample vessels as described above.

Figure 9:
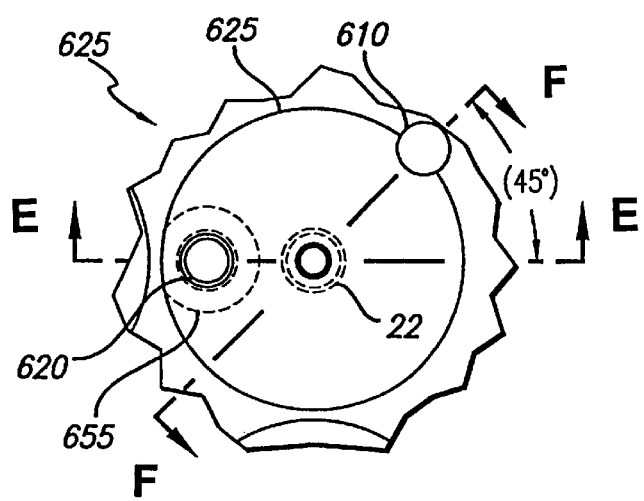
FIG. 9 is schematic showing a bottom view of a sample vessel area of a dispensing plate shown in FIG. 6 in accordance with the present invention.
Figure 10:
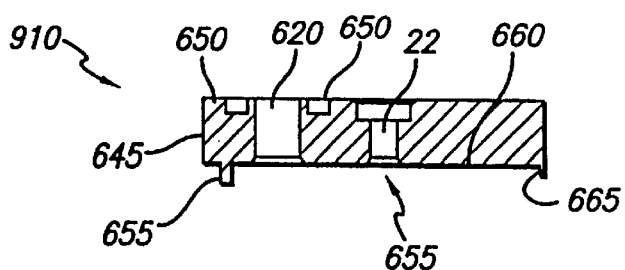
FIG. 10 is a schematic showing a cross sectional view of the sample vessel area shown in FIG. 9 taken along the line E—E in accordance with the present invention.
Figure 11:
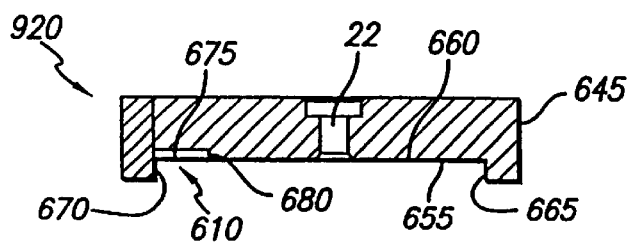
FIG. 11 is a schematic showing a cross sectional view of the sample vessel area shown in FIG. 9 taken along line F—F in accordance with the present invention.

In one embodiment, the gas distribution arrangement comprises two plates. The first plate, e.g., the bottom plate, typically comprises a plurality of sample vessel areas or indentations on the bottom surface. The indentations correspond to the array of sample vessels held in the container frame and serve to cap the sample vessels. FIGS. 9–11 illustrate features encompassed by the indentations, e.g., sample vessel area or indentation 625 on bottom portion 646. The indentations or recesses are also used, e.g., to immobilize the sample vessel within the container frame. Although the indentations are illustrated as circular, they are optionally any shape, e.g., to correspond to a variety of sample vessels.

One or more vents are typically positioned on the circumference of the sample vessel area, cap, or recess to allow gases and built up pressure to escape the sample vessel. FIG. 11 illustrates one embodiment of a venting space. However, other configurations of venting spaces and recesses are optionally constructed such that built-up pressure within sample vessels can escape without contaminating other sample vessels.

When the top surface of a sample vessel abuts the bottom surface of the gas distribution arrangement, gases, liquids, emulsions, or excess pressure built up in the sample vessel escape through a recess and/or venting space created in the gas distribution arrangement. Cross-contamination of these escaping elements is significantly reduced because a vertical edge in the bottom surface of the gas distribution arrangement separates each sample vessel from an adjacent sample vessel. Moreover, gas flow from the cannulas maintains a positive pressure within the sample vessel such that contaminants outside a particular sample vessel are not drawn in through the vent.

In some embodiments, the first plate comprises the plurality of cannulas that deliver gas to the sample vessels. The cannulas typically extend from the top surface of the plate, through the plate, and below the bottom surface of the plate. The cannulas are generally of sufficient length to reach within about 1 cm to about 0.1 cm of the bottom of the sample vessels. The cannulas open to the top surface of the plate, e.g., for gas to be distributed through the cannulas into the sample vessels. The cannulas are configured to be positionable in an array of sample vessels, e.g., held in a container frame.

In addition to the cannulas, the first plate optionally includes a plurality of apertures that correspond to the array of sample vessels. For example, the apertures optionally provide an opening through the first plate, through which fluids may be added into the sample vessels when the gas distribution arrangement is attached to a container frame.

The first plate is typically attached to a second plate, e.g., with screws or adhesives, which second plate typically comprises one or more gas inlets for providing gas flow into the cannulas of the first plate. The gas inlet opens into an interior space created between the second plate and the first plate, which interior space provides gas flow to the cannulas.

In addition, the second plate also comprises a plurality of apertures, e.g., to provide liquid access to the sample vessels. The apertures of the second plate typically align with or match the apertures on the first plate when the two plates are coupled. The apertures provide openings through which liquid can be added into the sample vessels in a container frame attached to the gas distribution arrangement. The apertures also serve as openings for an array of aspirators or dispensers that can be used to aspirate or dispense liquid into the sample vessels. In other embodiments, pipettes or syringes are used to draw samples or add nutrients, water, etc, e.g., through the apertures. The gas distribution arrangement also optionally comprises a lid for covering the apertures when a sealed environment is desired. The first plate and second plate together comprise a fermentor head or manifold for delivering gas or fluid to a plurality of sample vessels. More detailed examples are provided below.

A process controller is also optionally coupled to the fermentation apparatus of the invention, e.g., for controlling gas flow to the cannulas, for altering ratios of air to oxygen that are bubbled through the cannulas, for monitoring and controlling temperature, for directing the addition of various reagents, and the like. An automated process using a process controller is described in more detail in the examples below.

Other devices are also optionally coupled to the fermentor apparatus of the present invention. For example, dispensers, aspirators, centrifuges, and other processing devices are optionally coupled to the fermentor or configured for use with a container frame, e.g., so that samples can be processed in the same vessel in which fermentation is carried out. For example, a dispenser is optionally configured to dispense liquid into a plurality of sample vessels held in a container frame, e.g., through a plurality of apertures in a gas distribution arrangement. Aspirators are likewise optionally configured to coordinate with the container frame and gas distribution manifolds of the present invention.

A centrifuge is also optionally used in processing fermentation samples. For example, a centrifuge is optionally configured to accept the sample vessels as centrifuge tubes to avoid transferring of samples prior to centrifugation. For more information on centrifugation systems for use in the present invention, see, e.g., U.S. Ser. No. 09/780,589, entitled "Automated Centrifuge and Method of Using Same," by Downs et al, filed Feb. 8, 2001.

II. Methods of Fermenting Samples in a Multi-sample Fermentor

The multi-sample fermentors described above are used for simultaneously fermenting a plurality of samples, e.g., in a container frame that is transportable, e.g., to a processing station. The present invention also provides methods of using such fermentors, e.g., in conjunction with one or more processing steps. For example, the methods provided typically comprise providing a plurality of sample vessels in a container frame, each of which sample vessels contains a sample of about 50 to about 100 milliliters, more typically 65 ml. The samples are fermented in the sample vessels within the container frame.

Fermentation is used herein to refer generally to any process in which cells are used to convert raw materials, e.g., water, air, sugars, mineral salts, nitrogen sources, and the like, or enzyme substrates into desired products, e.g., proteins. Types of cells used include, but are not limited to, animal cells, yeast cells, and bacterial cells, e.g., *E. coli*, Bacillus, and the like. The cells are typically grown in a growth medium and then products are harvested. Fermenting typically involves simultaneously delivering gas to each of the sample vessels through a plurality of cannulas associated with the sample vessels, e.g., to aid growth of the cells. For example, the methods typically comprise attaching a fermentor head as described herein to a container frame containing the plurality of samples to be fermented. Once fermented, the samples are transferred to a post-processing station, e.g., a centrifuge. Typically, the post-processing station is configured to accept the same sample vessels in which the samples were fermented. In addition, some processing stations are configured to receive the container frame containing the sample vessels, e.g., a dispensing or aspirating station. An example method is described below and in FIGS. 4 and 5.

Figure 4:
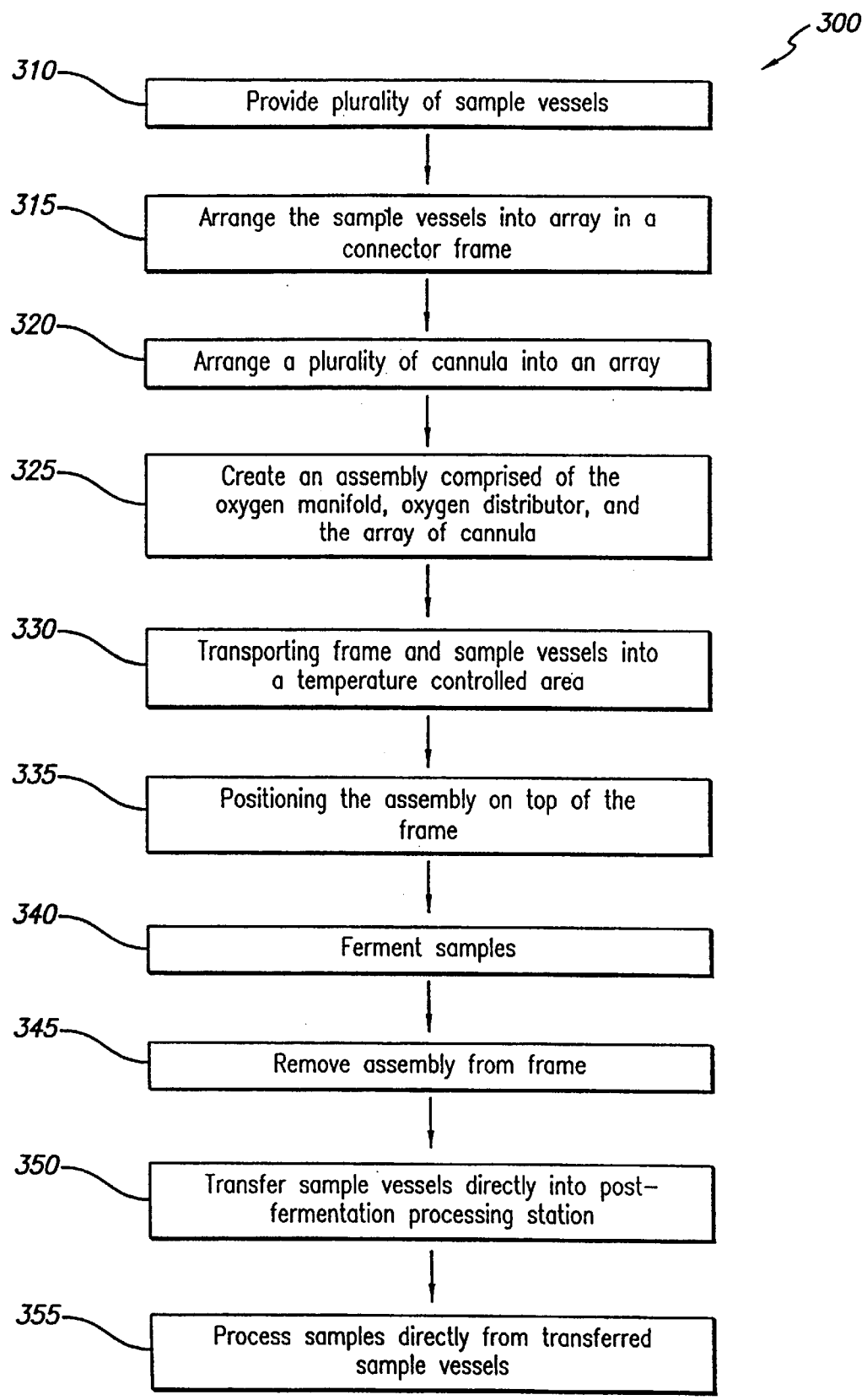
FIG. 4 is a block diagram of a fermentation method in accordance with the present invention.

FIG. 4 describes fermentation method 300 practiced in accordance with the present invention. Block 310 provides for a plurality of sample vessels 15. By providing a number of smaller volume fermentation vessels, this method is more advantageous than production scale fermentation methods that use bulk fermentation vessels, in that smaller volumes of growth medium are more predictable in their yield and nutrient needs than are standard production scale volumes that are utilized in bulk fermentation methods. The number of sample vessels that may be fermented at any one time is unlimited by the present invention, and instead is only limited either by the configurational practicalities of any one fermentation apparatus or by the number of sample vessels that may be handled by further processing steps in the production.

Block 315 arranges a plurality of sample vessels into an array, e.g., a rectangular 8 by 12 array. However, the array is optionally configured in any shape that is practicable for the fermentation apparatus. For example, sample vessels are optionally arranged in a rectangular array, a honeycomb configuration, or a linear array.

Block 320 arranges a plurality of cannula into an array corresponding to the sample vessels. According to the present invention, each cannula in this cannula array corresponds to an individual sample vessel in the sample vessel array, which are arranged in block 315. In one embodiment, the plurality of cannula is limited by the number of sample vessels arranged in block 315.

Block 325 creates a gas distribution arrangement for delivering oxygen and/or one or more other gases to a fermentation media in the sample vessels. For example, one embodiment fastens a cannula array to a gas distributor, which is connected to a manifold. The cannula array may be fastened by any means achieving a liquid-tight seal. For example, cannula are optionally connected via a union connector to a gas distributor. Alternatively, cannula are pneumatically connected to the distributor, or the cannula array and gas distributor are optionally molded as a single unit. In another embodiment, the distributor connects directly to a gas source without using a manifold. The methods of creating a gas distribution arrangement are optionally achieved using any method of uniformly delivering oxygen and/or one or more other gases from a gas source to a gas distributor such that gas is delivered to each individual sample vessel selectively or collectively by way of a corresponding cannula.

Block 330 transports the container frame containing the plurality of sample vessels to a temperature controlled area. Other methods known to those of skill in the art for controlling temperature are also contemplated within the present invention. For example, the container frame is optionally transported to a heated gel bath or a controlled temperature room used to maintain a constant temperature.

Block 335 positions the gas distribution arrangement created in block 330 on top of the container frame, e.g., using screws or by merely being placed on top and held in position by a groove assembly as shown in FIG. 14. From this configuration, the array of sample vessels is fermented in block 340.

Once fermentation is complete, block 345 removes the gas distribution arrangement from the container frame. The sample vessels are optionally transferred from the container frame directly to a post-fermentation processing station in block 350, e.g., by manipulating a gripping surface located on each sample vessel. This post-fermentation processing station includes any processing step where the fermentation product may be processed directly from the sample vessel. For example, the array of sample vessels may be transferred, either manually or robotically, from the container frame directly to an automated centrifuge. Alternatively, sample vessels may be transferred to an aspirating station or detecting station. In other embodiments, the sample vessels are not removed from the container frame but remain in it for further processing, such as dispensing or aspirating, using a dispenser or aspirator configured to coordinate with the array of sample vessels in the container frame.

In block 350, the fermentation product in the sample vessels is directly transferred into a post-fermentation processing station and in block 355 the fermentation product is directly processed in the sample vessels themselves. For example, in one embodiment, sample vessels are transferred directly to a centrifuge station in which the sample vessels are positioned directly inside the centrifuge such that the sample vessels act as centrifugation tubes and the fermentation product is centrifuged according to methods known in the art. Further processing steps such as aspirating, reagent dispensing, or detecting also optionally occur directly in the sample vessel used in the fermentation process. In this way, the fermentation vessel provides a sample vessel that holds the sample throughout the entire production process, thereby eliminating excess waste from transferring sample material from sample vessel to sample vessel as well as decreasing the cost of washing and sterilizing a fermentation apparatus in addition to sample vessels from each production process step. Other multiple process productions or analyses may also be practiced in accordance with the present invention.

In FIG. 5, block diagram 400 shows how the present invention is integrated into a multiple step, multiple process production. Block 410 depicts a processing station prior to fermentation. In one embodiment, fermentation broth and fermentation nutrients are added to sample vessels at prior processing station 410. Other processing steps involved in a multiple step production or analysis are also contemplated in accordance with the present invention. For example, bacteria colonization may occur in sample vessels at prior processing station 410. Example pre-processing steps include, but are not limited to, deionization, e.g., of solvents, pasteurization of materials, and mixing, e.g., of cell nutrient broths and the like. Such steps are typically used to process the raw materials, such as water, cell broths, sugars, nitrogen sources, and the like, used for the fermentation. Transporter 420, e.g., a robot, a technician, a conveyor belt, or the like, is optionally used to transfer the sample vessels from processing station 410 to a fermentation apparatus such as fermentation apparatus 100. Other embodiments of a fermentation apparatus practiced in accordance with this invention may also be used. For example, the fermentation apparatus shown in FIG. 14 or in FIG. 1 is optionally used.

It will further be appreciated that transporter 420 may transfer the sample vessels individually, in groups, or in an array configured for the fermentation apparatus. For example, in one embodiment, a container frame transports the sample vessel array to fermentation apparatus 100. Similarly, after fermentation, transporter 430 transports sample vessels from a fermentation apparatus to a post-fermentation processing station 410. In one embodiment, transporter 430 transports a container frame holding an array of sample vessels to a centrifuge processing station 410. Post-processing station 410 is optionally any other processing step occurring in a multiple process or analysis, such as an aspirating step, a dispensing step, or a detecting step. Example post-processing steps include, but are not limited to, precipitation, deionization, chromatography, evaporation, filtration, centrifugation, crystallization, drying, and the like. These steps are generally directed to purification, retrieval, and concentration of materials produced in the fermentation. In this manner, multiple processing steps are executed on each sample contained in the same sample vessel, thus enabling fermentation processes to be incorporated into high throughput or other multiple process systems. Example fermentation conditions are described below.

The present invention preferably uses fermentation conditions that lead to high level production of soluble proteins. These fermentation conditions may employ the use of high levels of yeast extract and bactotryptone (rich media, referred to as terrific broth or TB). Secondly, this media is optionally supplemented with 1% glycerol (additional carbon source). Lastly, the media preferably is typically buffered with 50 mM MOPS. Alternatively, a defined media comprising amino acids and 50 mM phosphate as opposed to MOPS is used. The first two additions allow the cells to be grown for up to about 10 hours without apparent loss of nutrients. The highly buffered media prevents the cells from being exposed to high levels of acid (low pH) which routinely occurs during fermentation.

Surprisingly less than 5% of human proteins expressed in normal Luria Broth or LB media, are typically found to be soluble. However, using the above media, 15–20% of human proteins expressed in *E. coli* now appear to be soluble.

In a preferred embodiment, the fermentation media is prepared as follows. TB media is prepared in 7L batches. Antibiotics are not added to TB media until the day it will be used for a fermentation run. To prepare the 7L bath, the following steps are performed: (1) Fill a clean 10L pyrex bottle with ~4L DI $H_2O$ or 18 megohm water, add a large stirbar; (2) Add 168 g Yeast Extract; (3) Add 84 g Tryptone; (4) Add 70 ml Glycerol; (5) Stir on stirplate until completely dissolved; (6) QS to 6.3L, e.g., with 18 megohm water; (7) Autoclave on the longest liquid cycle. Remove TB media from the autoclave as soon as possible, e.g., to prevent carmelization or burning of the carbon source and/or to allow for a quick cool down; (8) Store TB media at room temperature; and (9) Record process. TB Media is the same for all fermentor runs. However, Fermentor Media is not necessarily the same for all runs. For example, one difference in media is the antibiotic(s) added just before fermentation. On the same day of a fermentation run, the following may be added to TB media: (1) 350 mls of 1 M MOPS pH 7.6; (2) 7 ml Antifoam; (3) 7 ml 20 mg/ml Chloramphenicol; (4) 7 ml 100 mg/ml Ampicillin; (5) Add enough 18 megohm $H_2O$ to bring the volume up to 7L; (6) Write everything added to TB media on its label; (7) Cap tightly and shake bottle well; and (8) Record process. The above medium is only one of many possible choices known to those of skill in the art, which are optionally used with the present fermentors and methods.

When fermentation is complete, the sample vessels are transferred to a post-processing unit as described above, e.g., in the container frame, either manually or robotically. For example, a robot optionally removes the sample vessels from the container frame and places them, e.g., in a centrifuge.

III. EXAMPLES FERMENTATION SYSTEMS

Example Fermentor #1

In accordance with the present invention, an example fermentation apparatus is provided in FIG. 1. Fermentation apparatus 10 generally comprises sample holder arrangement 255, cannula assembly 80 and gas distribution arrangement 270. The illustrated fermentation apparatus 10 is configured to separately and simultaneously ferment multiple batch samples in sample vessels that are compatible with direct pre- and post-fermentation processing as described above.

Sample holder arrangement 255 is comprised of gripping surfaces 17, individual sample vessels 15, which typically form an array of sample vessels, such as array 110, a transportable container frame 250, and an array of placement wells 260 corresponding to array 110. Gripping surfaces 17 are optionally located on each individual sample vessel 15, which collectively form sample vessel array 110. It is preferable that gripping surface 17 resides on the bottom of each sample vessel, but gripping surface 17 is optionally located on any surface of the sample vessel that enables sample vessel 15 to be transferred to or from container frame 250 or another processing station.

The bottom of each individual sample well 15 is positioned within a placement well, e.g., placement well 257. The array of placement wells 260 preferably mirrors the configuration of array 110 and is embedded in transportable container frame 250.

By using transportable container frame 250, the entire array of sample vessels 110 is optionally transported to and from one fermentation processing station to another processing station in a multiple process production. In this illustrated example, transportable container frame 250 transports array of sample vessels 110 into a temperature controlled area 210 such as a water bath. In this embodiment, temperature controlled area 210 is comprised of water bath 240 in water bath container 215, which is controlled by water bath temperature controller 220 and temperature coil 230 immersed in water bath 240.

Figure 2:
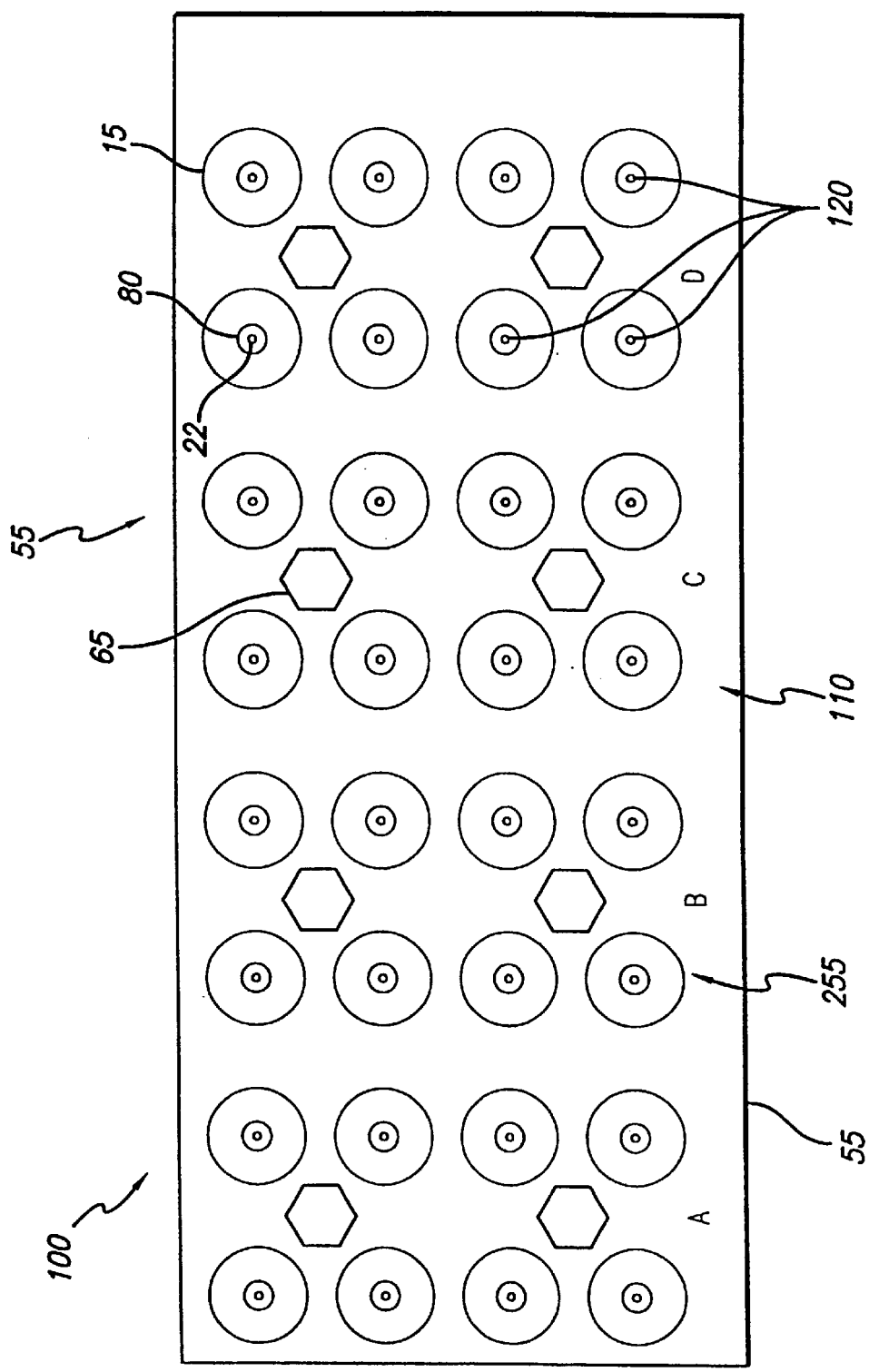
FIG. 2 is a schematic showing a top view of a fermentation apparatus in accordance with the present invention.
Figure 3:
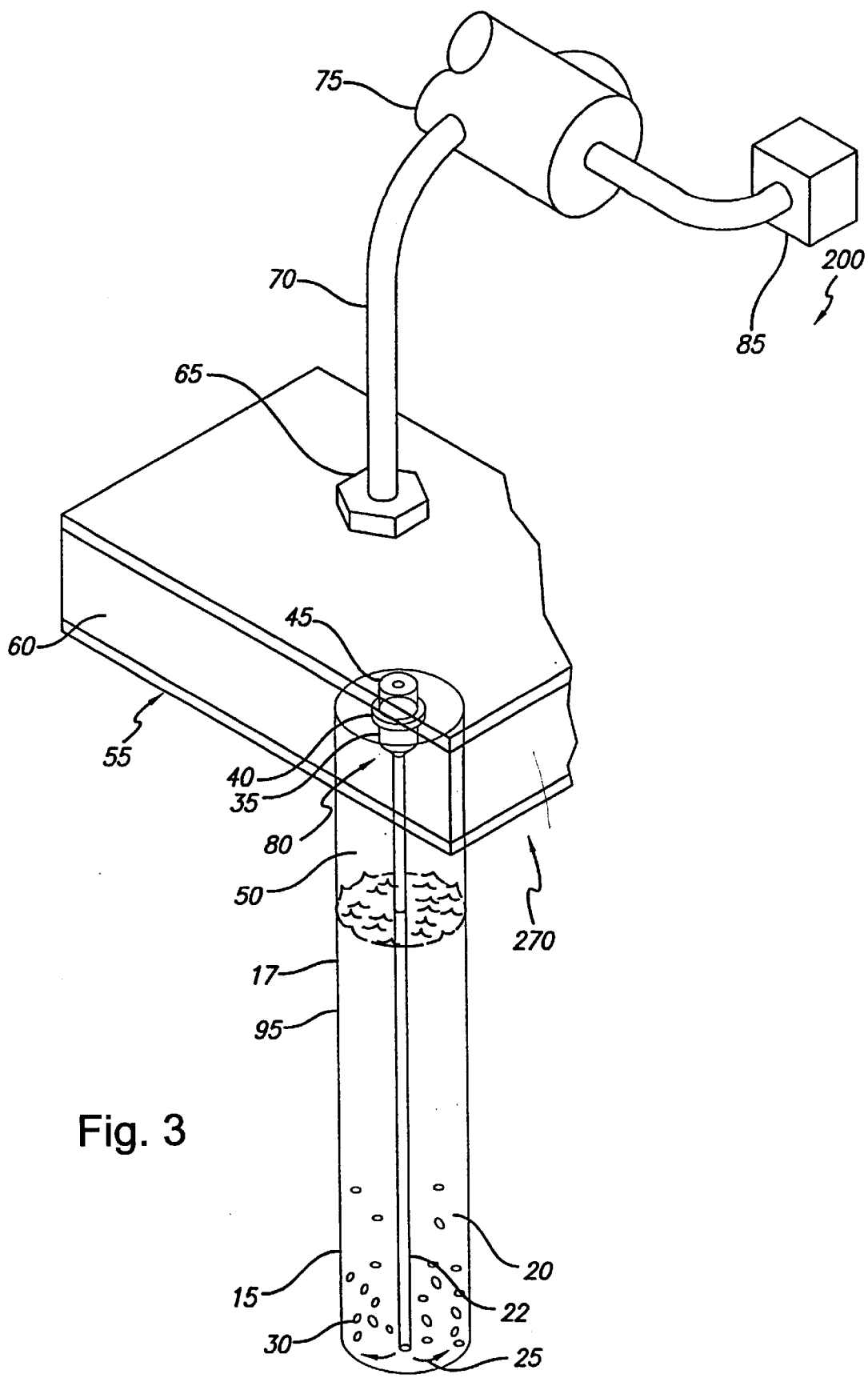
FIG. 3 is a schematic illustrating a perspective view of an individual fermentation sample vessel in accordance with the present invention.

In FIGS. 1–3, an example gas distribution arrangement is shown. Gas distribution arrangement 270 is comprised of gas source 85 connected to manifold 75. Conduit 70 connects manifold 75 to connector 65. Connector 65 connects manifold 75 to gas distributor 55.

In the embodiment illustrated in FIGS. 1 and 3, cannula assembly 80 is comprised of cannula array 120, which is composed of individual cannulas 22 that correspond to sample vessel array 110. Each individual cannula 22 is optionally connected by a fastener 35, which couples cannula 22 to a gas distribution arrangement 270. Cannula 22 preferably extends substantially to the bottom of each individual sample vessel 15 in order to increase aeration and mixing.

In another embodiment, each individual cannula is attached directly to gas distribution arrangement 270 in an airtight, liquid-tight manner. Eliminating the need for a fastener, this embodiment directly integrates cannula 22 into gas distribution arrangement 270, thereby decreasing the number of surfaces, grooves, and/or pockets available for possible bacterial contamination, and thus decreasing the opportunities for fermentation spoilage. Likewise, cannula 22, when integrated into a gas distribution arrangement 270 are optionally autoclaved with gas distribution arrangement 270, thereby eliminating the need to unfasten each cannula 22 separately before cleaning and sterilization. This convenience saves both time and money as well as adding to the uniformity of each batch. For example, the possibility for human error is minimized, because each cannula 22 does not have to be fastened individually before each fermentation run or unfastened individually prior to cleaning and sterilization. Also any non-uniformities in any one cannula 22 will be immediately apparent as an individual cannula 22 will be constantly associated with the same sample vessel in each run. Integrated cannula are shown in FIG. 14.

Referring to FIG. 3, gas, e.g., oxygen, is delivered from manifold 75 to all parts of distributor 55 through a hollow space 60 of distributor 55, thus oxygenating, if desired, the entire array of sample vessels 110. Oxygen and/or one or more other gases is delivered from distributor 55 through individual cannula 22, which is connected to distributor 55 by way of cannula assembly 80.

In one embodiment, cannula assembly 80 is comprised of a connector 45 on an inside face of distributor 55 as well as connector 40 on an outside face of distributor 55. Fastener 35 attaches individual cannula 22 to connector 40 on distributor 55. Arrows 25 depict oxygen and/or one or more other gases flowing from cannula 22 into fermentation medium 20 and producing gas bubbles 30. For example, gas source 85 is optionally coupled directly to dispensing plate 645 without the use of manifold 75, as illustrated in FIGS. 6 and 12. Likewise, cannula assembly 80 may be constructed by alternative methods. For example, as shown in FIG. 12, cannula 22 is attached directly to dispensing plate 645.

In this manner, the exact mixture of gases delivered from gas source 85 is uniformly distributed to each individual cannula assembly 80. Any gas distribution arrangement is optionally employed that uniformly delivers oxygen, an oxygen containing mixture, or another gas or gas mixture capable of fermenting the sample, from gas source 85 into sample vessel 15.

FIGS. 6 and 12 illustrate another embodiment of a gas distribution arrangement. Gas distribution arrangement 270 is comprised of a dispensing plate 645 directly attached to an array of cannula 120, that is configured without a manifold, manifold conduit, or manifold connector. In this embodiment, dispensing plate 645 is comprised of a bottom portion 646 and a top portion 647 (not shown). Inlet 630 delivers oxygen, an oxygen containing gas mixture, or another gas or gas mixture capable of fermenting the sample, to dispensing plate 645 from gas sources 85 (not shown).

Bottom portion 646 and top portion 647 are aligned and fastened together through apertures 640, e.g., to form an air-tight, liquid-tight seal. A hollow space exists between portions 646 and 645 through which gases are uniformly distributed to cannula array 120. Apertures 635 are used to fasten vertical supports to dispensing plate 645 that allow dispensing plate 645 to rest adjacent to array of sample vessels 110. Any suitable fastener may be used. In the illustrated example, screws connect upper portion 647 and bottom portion 646 to form dispensing plate 645. Screws also fasten aluminum legs to dispensing plate 645 as vertical supports.

FIGS. 9–11 illustrate yet another embodiment of a gas distribution arrangement. In this embodiment, cannula 22 is directly attached to bottom portion 646. Aperture 620 holds a dispensing tube 760 (not shown) for dispensing nutrients and other solutions into sample vessel 15. Aperture 620 is optionally used to access samples during the fermentation process, using, e.g., pipettes or syringes to draw samples or add nutrients, water, and/or the like into the sample vessels.

Fastening groove 650 enables dispensing tube 760 to be fastened to dispensing plate 645. Indentation 655 and vertical edge 665 create a circular recess that helps immobilize sample vessel 15 within sample vessel area 625. Although in this embodiment, indentation 655 is circular and corresponds to the shape of sample vessel 15, other suitable shapes may be used.

Vent 610 is positioned on the circumference of sample vessel area 625 and allows gases and built up pressure to escape sample vessel 15. Referring to FIG. 11, vent 610 creates venting space 675. Because vertical edge 670 is larger than vertical edge 665, venting space 675 occupies a deeper recess than recess 655. The difference in height between vertical edges 670 and 665 is equal to the height of vertical edge 680 and determines the depth of venting space 675. Other configurations of venting space 675 and recess 655 (and, accordingly, vertical edges 665, 670, and 680) may be constructed such that built-up pressure within sample vessel 15 can escape through venting space 675 without contaminating other sample vessels.

When the top surface of sample vessel 15 abuts surface 660, gases, liquids, emulsions, or excess pressure built up in sample vessel 15 may escape through recess 655 and venting space 675. Cross-contamination of these escaping elements is significantly reduced because vertical edge 670 separates sample vessel 15 from an adjacent sample vessel 15. Moreover, gas flow from cannula 22 maintains a positive pressure within sample vessel 15 such that contaminants outside sample vessel 15 are not drawn in through venting space 675 into sample vessel 15 by way of recess 625, 655, or 675. Other vents 610 may be configured such that excess gases, liquids, emulsions, or excess pressure may escape through vent 610 without cross-contaminating other sample vessels 15.

In another embodiment of gas distribution arrangement 270, illustrated in FIG. 2, array 110 is configured such that gas distribution arrangement 270 oxygenates, for example, each individual sample vessel 15 as opposed to utilizing a dispensing plate 645. Thus, array of sample vessels 110 is optionally oxygenated (or provided with other appropriate gas) collectively or individually by adjusting cannula assembly 80 for any individual sample vessel 15. For example, in one application, section A may be oxygenated (or provided with other appropriate gas) twice as long as section B.

In the illustrated example, cannula array 120 corresponds to sample vessel array 110, which is composed of individual sample vessels 15. Each individual sample vessel 15 also corresponds to an individual cannula assembly 80 which is connected to distributor 55. Oxygen and/or one or more other gases are delivered to distributor 55 through manifold connector 65. Oxygen and/or one or more other gases may be delivered through each cannula assembly 80, or selectively to certain assemblies 80. For example, cannula assemblies 80 in sections A and B may be utilized, while no gases flow to sections C and D.

Referring to FIGS. 3 and 12, gripping surface 17 allows for automated or manual transfer of sample vessel 15 to and from the fermentation apparatus or another processing station, e.g., upon conclusion of fermentation. In one embodiment, gripping surface 17 is magnetic such that a magnet attracts gripping surface 17 and transfers the sample vessel to another processing station. In another embodiment, a gripping mechanism grips the outer sides of the sample vessel to effect transfer. In yet another embodiment, gripping surface 17 is a lip at the top of the sample vessel. Other surfaces that may be gripped in order to transport the sample vessel to or from the fermentation processing station are within the scope of the present invention. For example, gripping surface 17 is optionally on the inside, outside, top or bottom of sample vessel 15. In other embodiments, the samples are held in place and transported with the aid of a gripper structure.

FIG. 12 illustrates one embodiment of a gas distribution arrangement. Gas distribution arrangement 270 and cannula 22 are used together to provide gas to a sample vessel. In this example, oxygen, a mixture of oxygen and other gases, or another gas or gas mixture is introduced into dispensing plate 645 through inlet 630. Fasteners such as screws connect and align upper portion 647 to bottom portion 646 through apertures 640. Dispensing tube 760 and cannula 22 are directly attached to dispensing plate 645 and can be replaced by unfastening portions 646 and 647, replacing either or both dispensing tube 760 or cannula 22, and refastening portions 646 and 647. It is preferable for dispensing tube 760, cannula 22, inlet 630, and portions 646 and 647 to remain fastened together such that these elements are autoclaved as one unit. This allows for significant sterilization without the time and cost expense of dismantling arrangement 270 after each fermentation in order to separately sterilize each element.

In the illustrated example, a top surface of individual sample vessel 15 abuts directly onto surface 660 within sample vessel area 625. The top surface of sample vessel 15 is positioned within recess 655. Surface 660 preferably is not in contact with the entire circumference of the top surface of sample vessel 15. Also preferably, vent 610 is positioned adjacent to surface 660 such that a gap 672 exists between surface 660 and the vertical edge of sample vessel 15, thereby creating a passage for excess gases, emulsions, or pressure to escape from sample vessel 15 through venting space 675. Gas flow through cannula 22 provides sufficient pressure such that contaminants are not drawn into sample vessel 15 through venting space 675.

Example Fermentor #2

FIGS. 13–21 illustrate another embodiment of the fermentor apparatus of the present invention. Generally, the apparatus comprises a container frame comprising placement wells, and a gas distribution arrangement comprising a cannula array. Each piece is described in more detail below and by reference to the figures.

Container frame 1300, as shown in FIG. 13, comprises bottom 1310 and top portion 1320 connected by side portions 1325 and 1330. The container is easily transportable, e.g., by grasping handles 1335 and 1340 which are attached to sides 1325 and 1330. Each side 1325 and 1330 has two grooves 1345 which can each receive a pin for securing a gas distribution arrangement, such as that shown in FIG. 16, e.g., using pins 1480. Top portion 1320 and bottom portion 1310 together form an array of placement wells 1350. Bottom portion 1310 of the container frame has a plurality of indentations that serve as bottoms for the placement wells, in which sample vessels are placed. For example, container frame 1300 comprises an 8 by 12 array of placement wells. Top portion 1320 comprises a matching array of holes 1360 which holes receive the sample vessels into the container frame and hold them in position within the container frame. Together holes 1360 and indentations 1355 in container frame 1300 form a rack for holding a plurality of sample vessels, e.g., tubes. Although holes 1360 are shown as circles, the shape is optionally configured to receive any desired sample vessel.

FIG. 14 illustrates a gas distribution arrangement coupled to container frame 1300. The gas distribution arrangement comprises four pins 1480 which slide into grooves 1345 to hold the gas distribution arrangement in place over the container frame. As shown in FIG. 14, the gas distribution arrangement comprises first plate 1465 and second plate 1470, which are typically fastened together, e.g., using screws or pins. An optional lid, e.g., lid 1460, is also shown. In addition, the gas distribution arrangement comprises handles 1410 and 1420 attached to second plate 1470 for easy positioning and removal of the gas distribution arrangement.

Inlets 1430 and 1440 provide gas inlets to the gas distribution arrangement, which gas inlets typically receive gas from a gas source and deliver it, e.g., to a plurality of cannulas. Typically, the plurality of cannulas is attached to the gas distribution arrangement, e.g., as part of the first plate. For example, in the illustrated embodiment, cannula 1450 is part of first plate 1465 and extends from the top of the first plate, through the first plate and below, such that the cannula is positionable inside a placement well, e.g., well 1350, or inside a sample vessel positioned within placement well 1350.

Typically, first plate 1465 comprises the cannula array and a plurality of apertures. The apertures of the first plate align with a set of apertures on the second plate to provide access to the sample vessels within the placement wells. The cannula array is optionally molded as part of the first plate or separately formed and then attached to the first plate. For example, an additional set of apertures is optionally present in the first plate to accept the array of cannula, e.g., which are received into the aperture and secured using o-rings.

Figure 18:
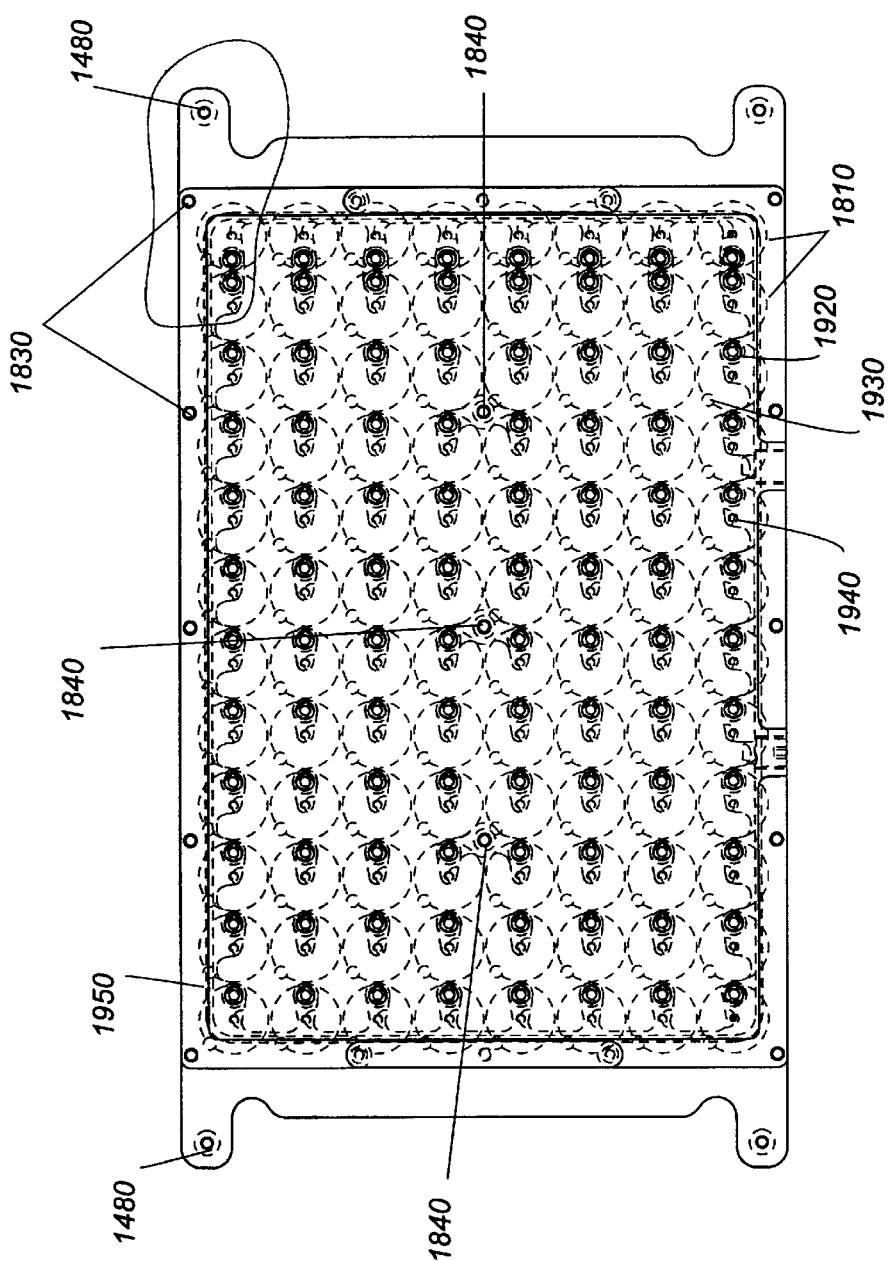
FIG. 18 is a schematic drawing that illustrates a bottom view of gas distribution arrangement as shown in FIG. 14.
Figure 19:
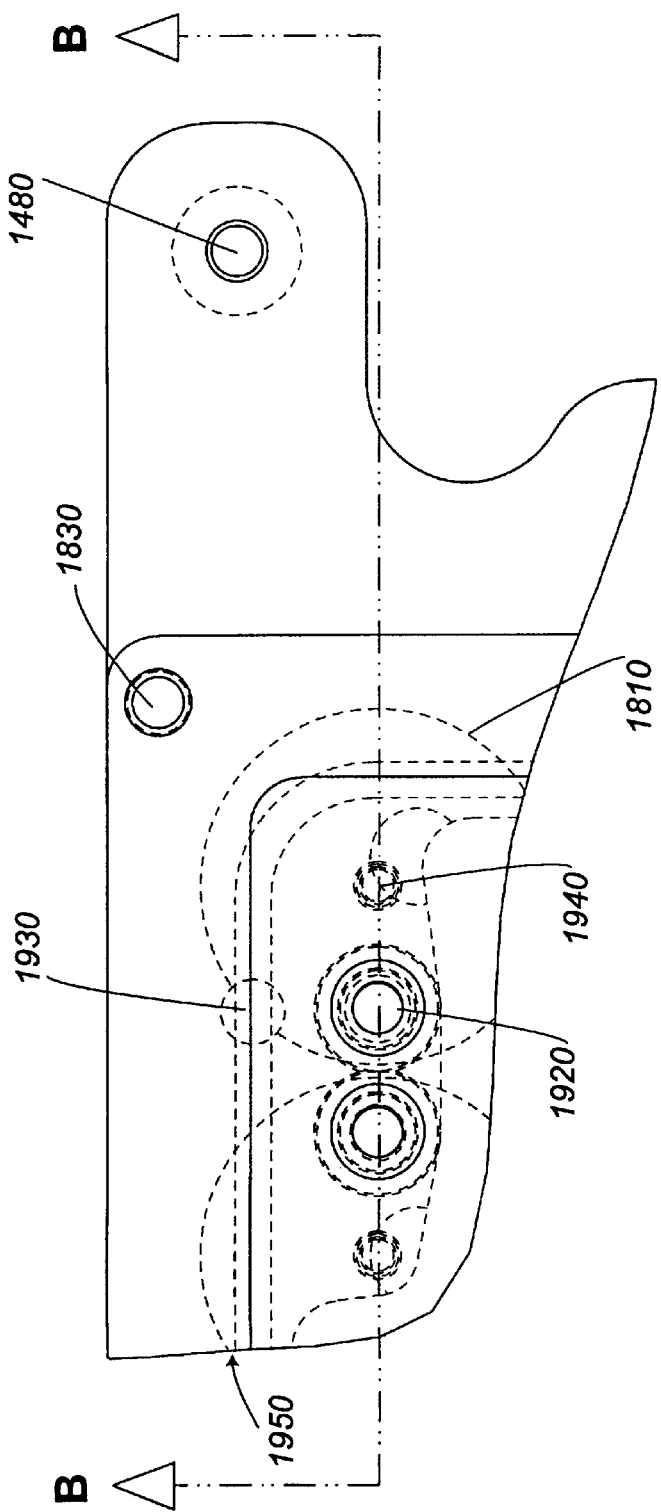
FIG. 19 is a detail illustration from FIG. 18.

FIG. 18 illustrates the bottom surface of first plate 1465. For example, on the bottom surface of the first plate, an array of sample vessel areas 1810 or indentations are used to cap the sample vessels and provide venting space as described above in Example 1. Each sample vessel area comprises an aperture to provide access to the sample vessel positioned with the associated placement well, a cannula associated with each placement well for delivering gas into each sample vessel positioned within the well, and a vent for relieving pressure build up during fermentation. In addition, FIG. 18 illustrates apertures 1830 and 1840, which are used, e.g., to attach the second plate to the first plate, e.g., via a set of screws. FIG. 19 provides a detail drawing of a portion of FIG. 18 illustrating aperture 1920, vent 1930, and cannula 1940. In addition, FIG. 19 illustrates gasket or o-ring 1950 that serves to provide a seal between the first and second plates.

Figure 21:
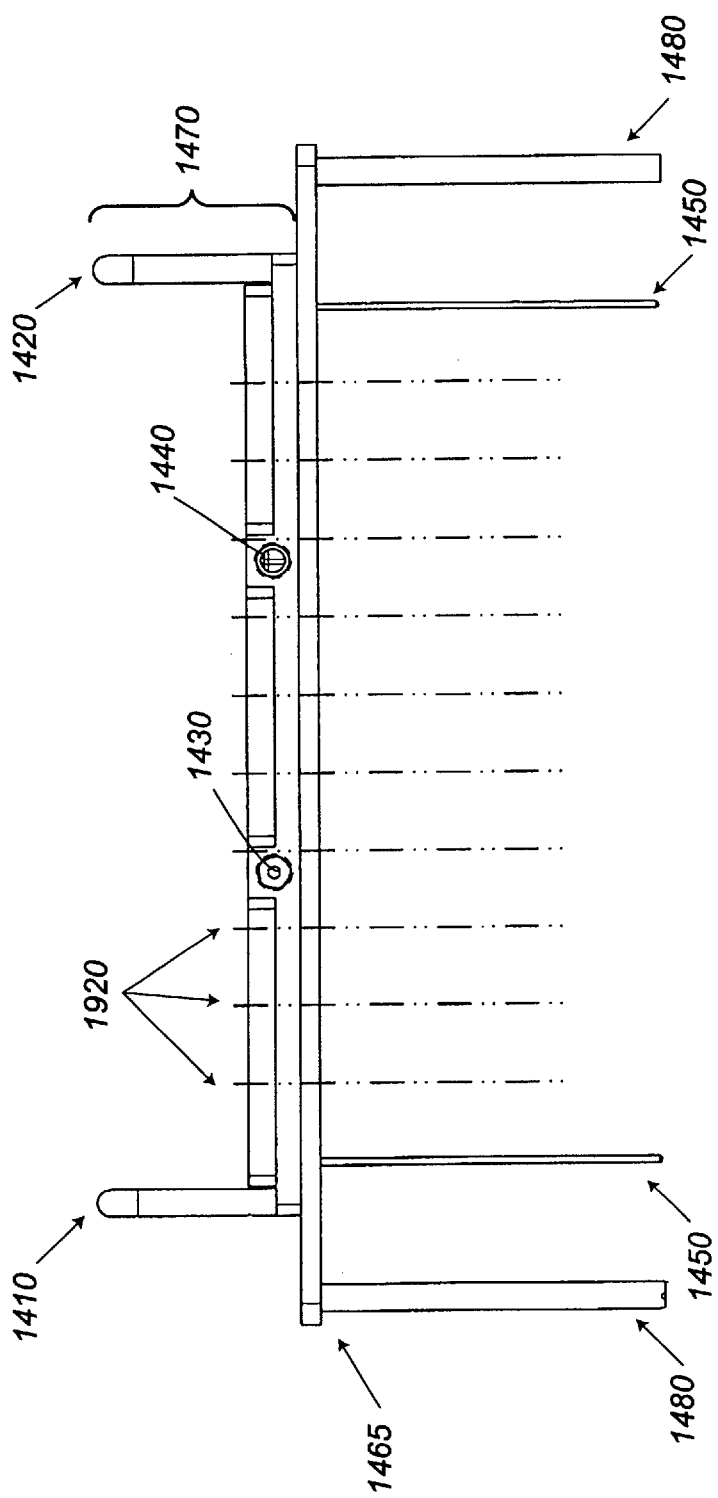
FIG. 21 is a schematic drawing that provides a side view of the gas distribution arrangement as shown in FIG. 14.

Second plate 1470 typically comprises a set of apertures as described above, which correspond to the set of apertures in plate 1465. These apertures are used, e.g., for liquid dispensing and/or venting. The apertures in the two plates connect to form a passageway that extends through both plates for access to placement wells 1350. The apertures are closed off from the interior space and can be capped using a lid as shown in FIG. 14 when a sealed system is desired. In addition, second plate 1470 typically comprises the gas inlet, e.g., inlet 1430, and an interior space through which gas is flowed. FIG. 21 provides a side view of the gas distribution arrangement as shown in FIG. 14. For example, FIG. 21 shows cannulas 1450 extending below the first plate into the placement wells and apertures 1920 extending through the first plate and the second plate.

Figure 20:
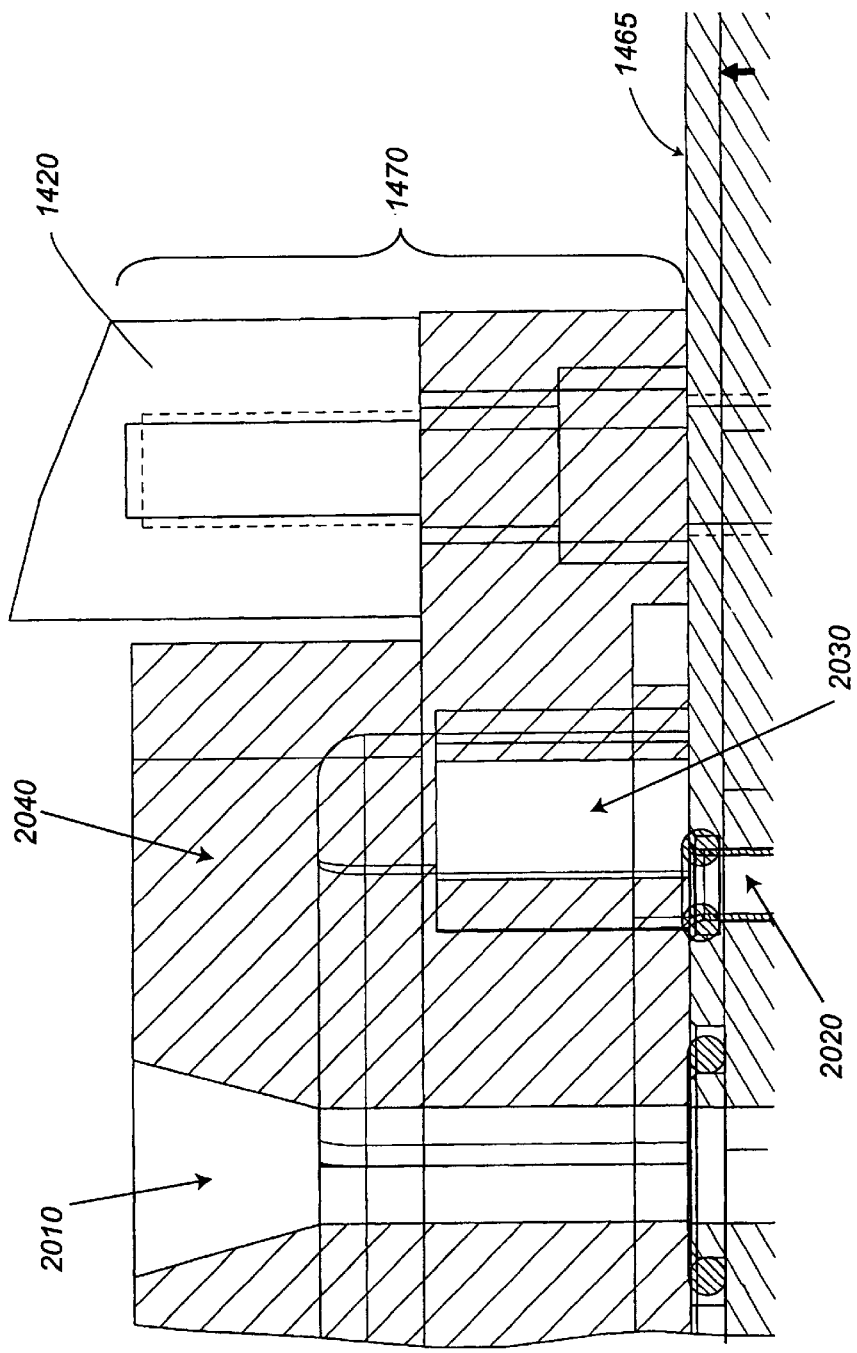
FIG. 20 is a schematic drawing illustrating a cross-sectional view of a gas distribution arrangement including top and bottom plates taken along line B—B of FIG. 19.

FIG. 20 illustrates a cross-sectional view of the gas distribution arrangement of FIG. 14, which comprises a first and a second plate. Top plate 1470 is attached to bottom plate 1465, e.g., using screws positioned through apertures 1830, and 1840. The first plate, which is on the bottom, comprises apertures 2010 and cannulas 2020. The apertures are open holes in first plate 1465, which align with similar apertures in second pate 1470, the top plate. The cannula are inserted into the first plate through another set of apertures secured with O-rings, e.g., to form a seal between the top and bottom plates. The cannulas extend from the top surface of plate 1475 into placement wells 1350 such that they are easily positioned in an array of sample vessels held in the placement wells. Cannula 2020 does not extend into plate 1470, but abuts it. Adjacent to where cannula 2020 abuts plate 1470 is venting space 2030 which couples the cannula to interior space 2040 of the top plate through which interior space gas flows in through an inlet, e.g., inlet 1430.

Figure 15:
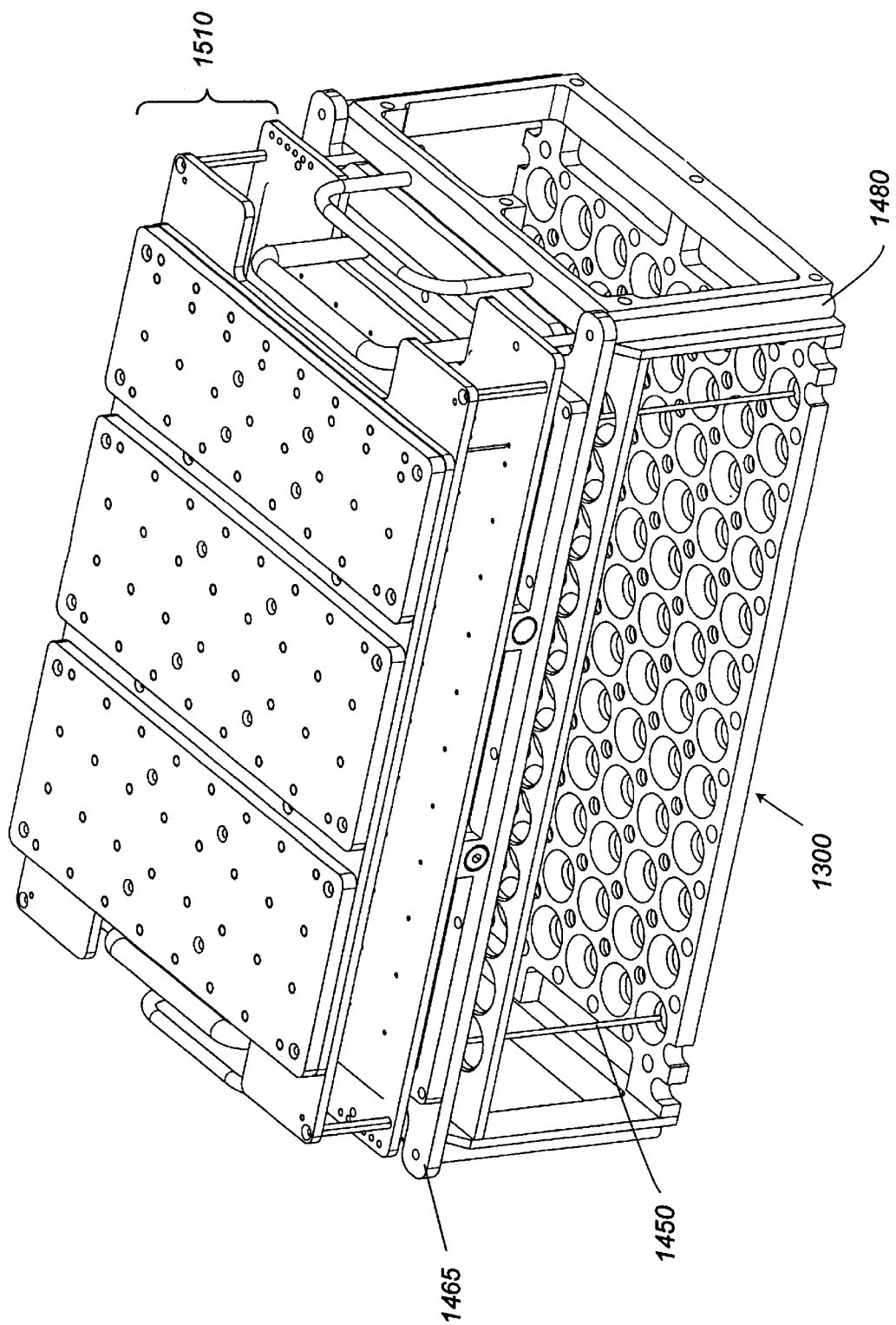
FIG. 15 is a schematic drawing that illustrates the container frame of FIG. 13 coupled to an alternative gas distribution arrangement configured for liquid additions.
Figure 16:
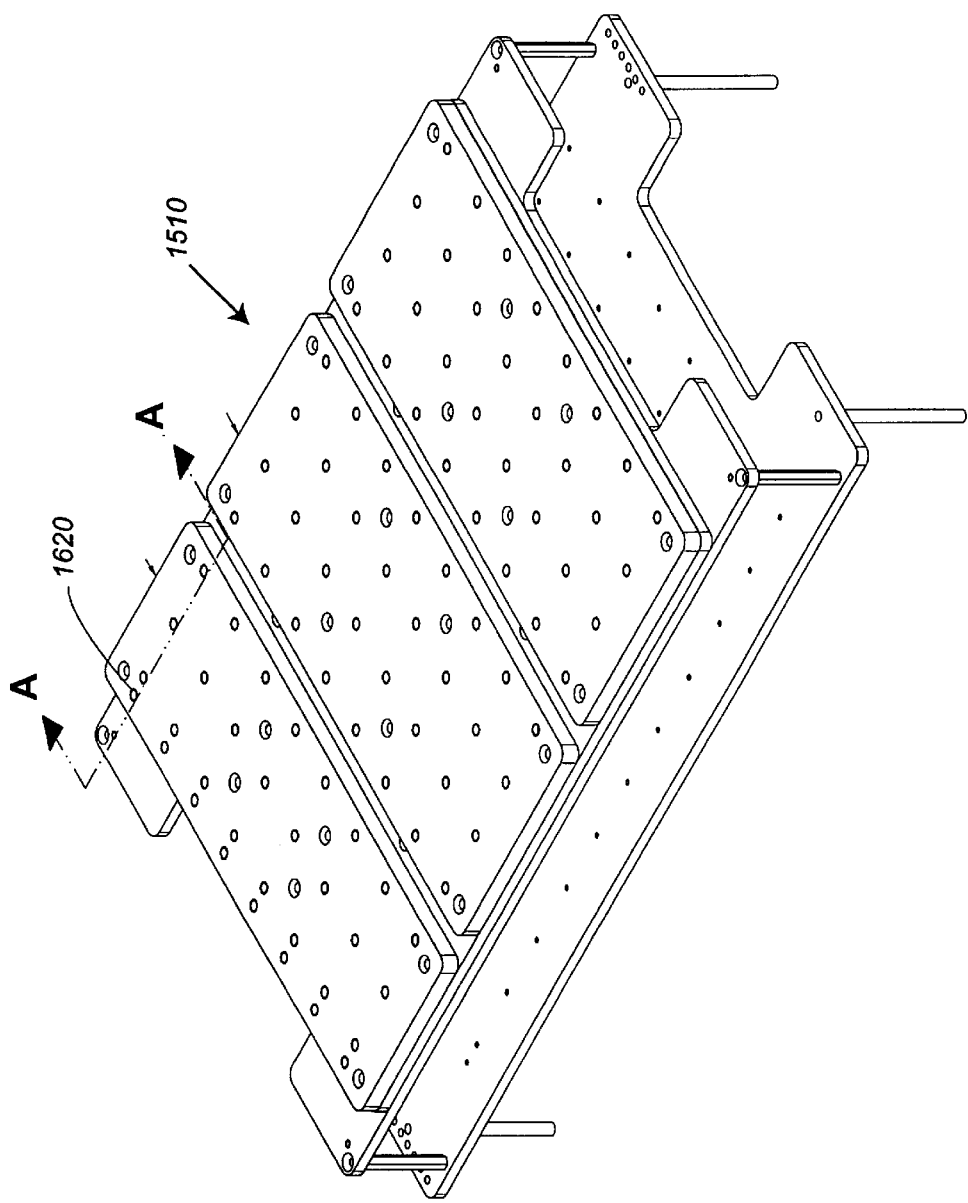
FIG. 16 is a schematic drawing that illustrates the gas distribution manifold with a liquid addition capacity of FIG. 15.
Figure 17:
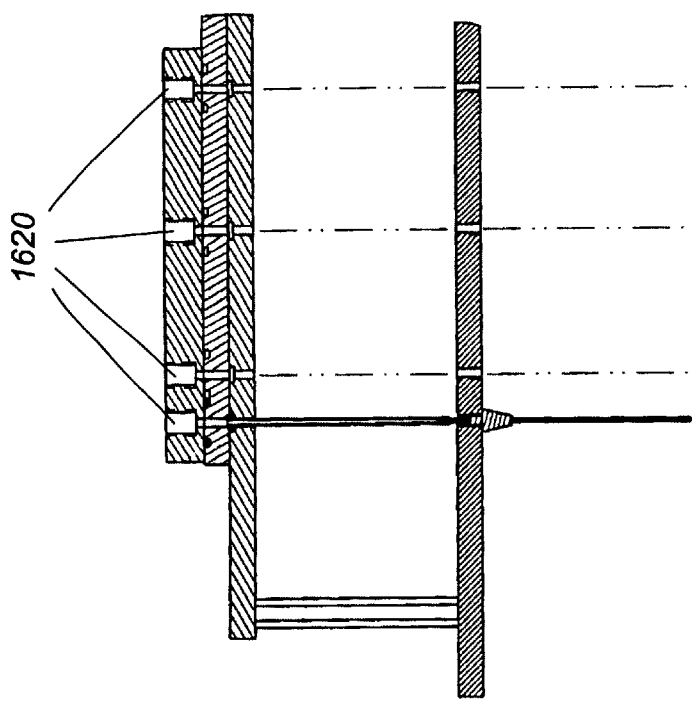
FIG. 17 is a schematic drawing that illustrating a cross-sectional view taken along line A—A of FIG. 16.

FIG. 15 illustrates a container frame with a liquid addition manifold assembly coupled to it. Container frame 1300 is shown with first plate 1465 positioned on top using pins 1480. Second plate 1470 is positioned on top of the first plate and liquid addition manifold 1510 is shown on top of the second plate of the gas distribution system. The liquid addition manifold is optionally used to add liquid into the sample vessels, e.g., through corresponding sets of apertures in the first and second plate. FIG. 16 illustrates liquid addition manifold 1510 in more detail, e.g., apertures 1620, which align with apertures on the first and second plates of the gas distribution arrangement. Apertures 1620 are used to deliver liquid reagents into the sample vessels contained in the apparatus. Manifold 1510 is placed, e.g., using pins, on top of the gas distribution system. In addition, FIG. 17, a cross-sectional view of the liquid addition manifold along line A-A, illustrates how pipettes or additional cannulas are used to dispense liquid into the sample vessels.

Example System 3—an Automated System

Figure 7:
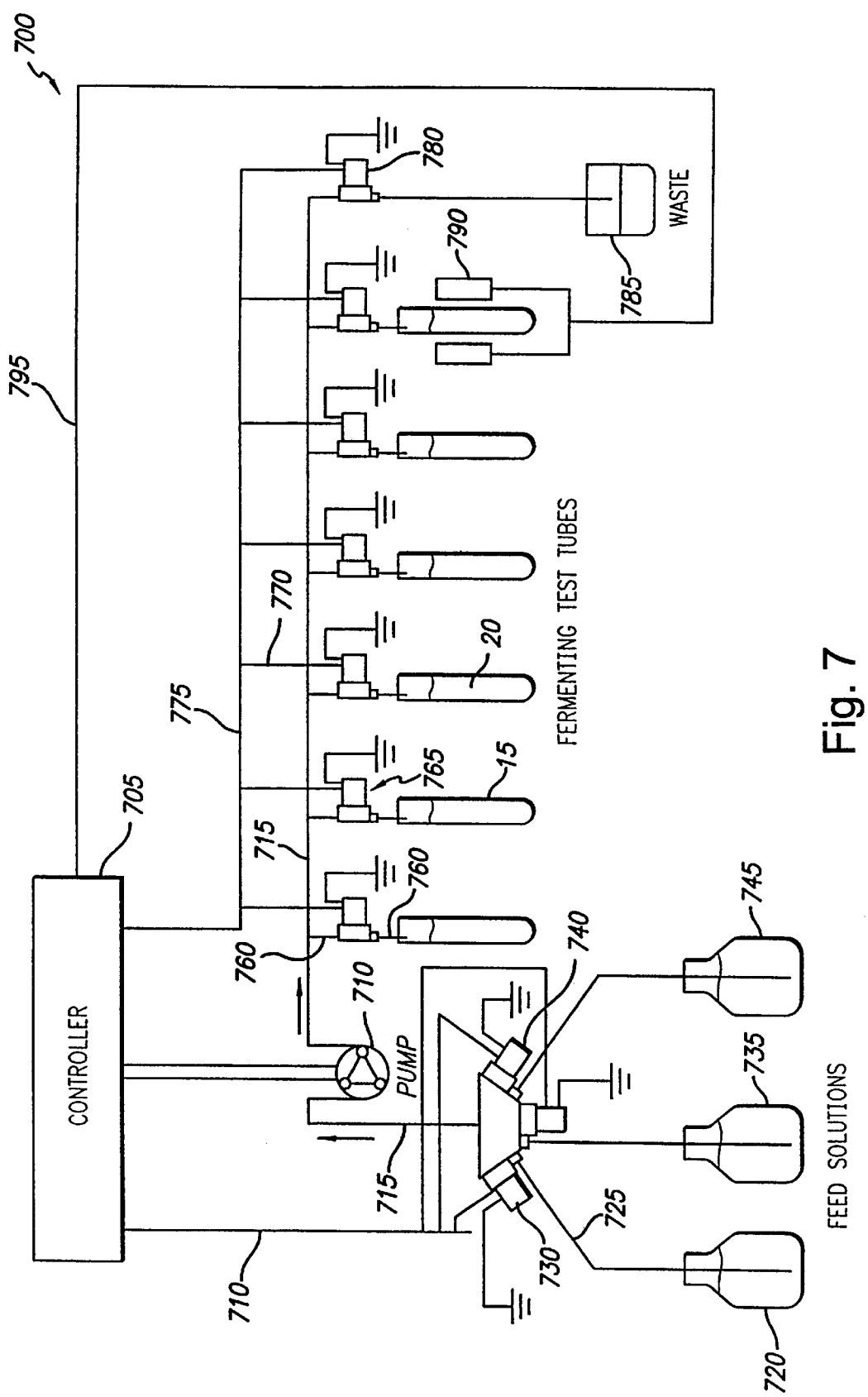
FIG. 7 is an automated fermentation assembly in accordance with the present invention.

FIG. 7 illustrates an example of an automated fermentation apparatus. Process controller 705 monitors and controls various components of apparatus 700 and preferably is a programmable computer with an operator interface. Alternatively, process controller 705 is any suitable processor that coordinates multiple components of apparatus 700, such as timing mechanisms, adding solutions, adjusting temperature, adjusting gas flow rates and gas mixtures, detecting measurements, and/or sending an alarm or notification prompting operator intervention. Electronic couples 710, 755, and 795 connect various components of fermentation apparatus 700 to process controller 705. For example electronic couple 710 enables controller 705 to start, stop, and monitor solution flow from feed solutions 720, 735, and 745. Likewise, electronic couple 775 enables controller 705 to start, stop and monitor reagent dispensing into sample vessels 15. Electronic couple 795 also enables controller 705 to transmit and receive information from sensors 790 as well as monitor and adjust temperature controlled areas. Other coupling devices are also optionally used in the present invention.

In one embodiment of fermentation apparatus 700, feed solutions 720, 735, and 745 are pumped (either singly, in combination, sequentially, or collectively) from individual feed tubes 725 into dispensing tube 715. Selecting the appropriate solenoid determines which feed solution is pumped through dispensing tube 715. For example, solenoid 730 controls flow from feed solution 720 through feed tube 725. In another application, a mixture of feed solutions 720 and 735 are simultaneously pumped into dispensing tube 715. In another application, feed solution 720 is fed into dispensing tube first, followed by an incubation period (directed by controller 705), followed by feed solution 735 being pumped into dispensing tube 715. Different combinations of feed solutions are optionally used and more or fewer feed solutions may be used with apparatus 700 according to any desired application.

Using pump 710, which is optionally a peristaltic pump, dispensing tube 715 transfers feed solution to an individual dispensing tube 760. Each individual dispensing tube 760 corresponds to an individual sample vessel 15 and tube 760 is positioned such that feed solution 720, for example, is transferred volumetrically from dispensing tube 760 into its corresponding sample vessel 15 once solenoid 765 is opened. Each solenoid 765 corresponds to an individual sample vessel 15. Volumetric dispensing of feed solutions is controlled by process controller 705 which preferably controls the amount, the rate and the time of dispensing. Dispensing tube 760 is optionally composed of plastic, metal, or any material that is non-reactive to the feed solution being dispensed.

In one embodiment, delivery solenoids 765 work in conjunction with pump 710 and controller 705 to deliver multiple feed solutions such as feed solutions 720, 735, and 745 into individual sample vessels 15. Each solenoid 765 corresponds to a sample vessel 15 and the solenoids 765 are manifolded together and fed by the output of a single peristaltic pump 710. Each solenoid 765 preferably opens sequentially in order to dispense a volumetric amount of feed solution 720. However, parallel addition is also contemplated within the present invention.

In one embodiment, feed solution 720 introduces nutrients into fermentation medium 20 through dispensing tube 715 using pump 710 and solenoid 765 to deliver solution 720 to individual dispensing tube 760. After addition of feed solution 720, solenoid 730 is closed and solenoid 740 corresponding to rinse solution 745 opens. Pump 710 delivers rinse solution 745 through dispensing tube 715, thereby rinsing dispensing tube 715 with solution 745, which is then flushed into waste container 785. Solenoid 780 controls flow from dispensing tube 715 into waste container 785. Feed solution 735 is then pumped through dispensing tube 715 and dispensed through tube 760. Dispensing tube 715 is rinsed again with rinse solution 745 before another addition. Solenoids 765 are preferably located very near to dispensing tube 760 in order to minimize dead volume downstream. In this way, dispensing tube 715 accurately delivers a known amount of feed solution 720 and 735 without cross contaminating or fouling the next or different addition of feed solution through dispensing tube 715. Accordingly, each addition is volumetrically precise with a minimal, known amount of feed solution from a previous addition diluting the next addition. In this way, feed solutions such as additional nutrients, trace minerals, vitamins, sugars, carbohydrates, nitrogen containing compounds, evaporating liquids, pH balancing compounds, buffers, and other liquids may be added to fermentation media 20 in an automated, yet highly precise manner.

Coordinated by process controller 705, various components may be activated either at pre-determined time intervals or in response to the measurement of some physical property within sample vessel 15. For example, in one embodiment, an operator programs process controller 705 to incubate sample vessels 15 for a pre-determined time period at a particular temperature, add a desired amount of feed solution 720, and incubate further for another pre-determined time period at a different temperature. Any suitable combination of fermentation conditions may be programmed into process controller 705, which optionally comprises a computer, computer network, other data input module, or the like.

In a preferred embodiment, process controller 705 coordinates temperature control, the addition of feed solutions, adjustment of gas rates and gas mixtures, incubation periods, and rinsing in response to data received from sensors 790. Sensors 790 are optionally located inside or outside of individual sample vessels 15. Sensors 790 can detect color changes spectrophotometrically, monitor evaporation rates, measure changes in optical density, detect light changes photometrically, detect pH changes, electrolytically measure redox potentials, monitor temperature fluctuations, or detect other physical changes and transmit this data to process controller 705. In response, process controller 705 accordingly adjusts various components of apparatus 700. For example, by measuring the redox potential, sensors 790 detect when a fermentation sample is being over-oxygenated or over-provided with another gas and process controller 705 accordingly adjusts the gas flow or gas mixture ratio. As another example, process controller 705 can respond to a change in pH, as detected by sensors 790, by adding a pH buffer from feed solution 720. In one embodiment, maximum protein expression may be detected by monitoring light emission, at which point fermentation is halted to minimize wasting fermentation resources after optimum fermentation yield has been reached.

Because of the uniformity of each fermentation medium 20, cannula 22, and dispensing of feed solutions 720, very few, for example, one, sensor 790 is all that is necessary to monitor the entire array of sample vessels 110. Alternatively, when sample vessels 15 contain different fermentation media 20 or undergo different fermentation conditions, numerous sensors 790 are optionally employed.

The above automated process is optionally used in conjunction with any fermentor apparatus or method to known to those of skill in the art. In particular, it is useful when practicing fermentation using the fermentors presented herein. However, it is noted that the examples presented herein are provided for purposes of illustration and not of limitation. While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations and other uses for the present invention are also contemplated. It is also noted that equivalents for the particular embodiments discussed in this description may be used in the invention as well.

All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A fermentor head for multiple sample fermentation, the fermentor head comprising:
   (a) a dispensing plate that comprises a top portion and a bottom portion, wherein the bottom portion and the top portion are joined together such that a hollow space exists between the top portion and the bottom portion;
   (b) an array of sample vessel areas located in a bottom surface of the bottom portion, which sample vessel areas each comprise a recess and are positioned to correspond to an array of sample vessels;
   (c) an array of cannulas that are in fluid communication with the hollow space and protrude from a bottom surface of the dispensing plate through the sample vessel areas, wherein at least one cannula of the array of cannulas extends into a liquid in a sample vessel when the sample vessel is positioned in a sample vessel area through which the cannula protrudes; and
   (d) a gas inlet in fluid communication with the hollow space for delivering gas into a plurality of sample vessels via the cannulas during fermentation.

2. The fermentor head of claim 1, wherein the dispensing plate further comprises an array of apertures for accessing samples during fermentation.

3. The fermentor head of claim 1, wherein the array of cannulas comprises an 8 by 12 array.

4. The fermentor head of claim 1, wherein the array of cannulas comprises at least 96 cannulas.

5. The fermentor head of claim 4, wherein the array of cannulas comprises 96, 384, or 1536 cannulas.

6. The fermentor head of claim 1, wherein the cannulas extend 15 to 16 centimeters below the bottom surface of the dispensing plate.

7. The fermentor head of claim 1, wherein at least one sample vessel area comprises a size sufficient to hold a sample vessel having a volume of 50 to 200 ml.

8. The fermentor head of claim 7, wherein the recess is of a size sufficient to hold a sample vessel having a volume of 50 to 100 ml.

9. The fermentor head of claim 1, wherein the cannulas deliver gas adjacent to a bottom of the sample vessels during fermentation.

10. The fermentor head of claim 1, wherein the gas inlet delivers oxygen or nitrogen into the hollow space of the dispensing plate, thereby providing oxygen or nitrogen to the sample vessels via the cannulas during fermentation.

11. The fermentor head of claim 1, wherein each of the cannulas comprise at least three passages.

12. The fermentor head of claim 1, wherein the cannulas are adapted to deliver gas, deliver fluid, or aspirate fluid from the sample vessels during fermentation.

* * * * *